(12) United States Patent
Sambhara et al.

(10) Patent No.: US 8,163,545 B2
(45) Date of Patent: Apr. 24, 2012

(54) VACCINE AGAINST PANDEMIC STRAINS OF INFLUENZA VIRUSES

(75) Inventors: Suryaprakash Sambhara, Atlanta, GA (US); Jacqueline Katz, Atlanta, GA (US); Mary Hoelscher, Atlanta, GA (US); Suresh K. Mittal, West Lafayette, IN (US); Dinesh S. Bangari, West Lafayette, IN (US)

(73) Assignees: United States of America as represented by the Secretary of the Department of Health and Human Services, Centers for Disease Control and Prevention, Washington, DC (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 12/646,078

(22) Filed: Dec. 23, 2009

(65) Prior Publication Data

US 2010/0158939 A1 Jun. 24, 2010

Related U.S. Application Data

(63) Continuation of application No. 11/911,189, filed as application No. PCT/US2006/013384 on Apr. 10, 2006, now abandoned.

(60) Provisional application No. 60/670,826, filed on Apr. 11, 2005.

(51) Int. Cl.
| | |
|---|---|
| *C12N 15/00* | (2006.01) |
| *A61K 39/145* | (2006.01) |
| *A61K 39/295* | (2006.01) |
| *C12N 15/09* | (2006.01) |

(52) U.S. Cl. .................................. 435/320.1; 424/209.1
(58) Field of Classification Search ........................ None
See application file for complete search history.

(56) References Cited

U.S. PATENT DOCUMENTS

| | | | |
|---|---|---|---|
| 6,348,450 B1 | 2/2002 | Tang et al. | |
| 6,716,823 B1 | 4/2004 | Tang et al. | |
| 6,770,479 B1 | 8/2004 | Lee et al. | |
| 2002/0192185 A1 | 12/2002 | Mittal et al. | |
| 2004/0009183 A1 | 1/2004 | Lee et al. | |
| 2004/0197914 A1 | 10/2004 | Wasilko et al. | |
| 2007/0003576 A1 | 1/2007 | Gambotto et al. | |

FOREIGN PATENT DOCUMENTS

| | | |
|---|---|---|
| WO | WO 00/66179 | 11/2000 |
| WO | WO 03/091438 | 11/2003 |
| WO | WO 2006/063101 | 6/2006 |
| WO | WO 2006/113214 | 10/2006 |

OTHER PUBLICATIONS

Wood et al. Arch Virology, 1993, vol. 130, pp. 209-217.*

Ha et al. The EMBO Journal 2002, vol. 21, No. 5, pp. 865-875.*
Abe et al., "Baculovirus Induces an Innate Immune Response and Confers Protection from Lethal Influenza Virus Infection in Mice," *J. Immunol*, 171: 1133-1139 (2003).
Alkhatib et al., "High-Level Eucaryotic In Vivo Expression of Biologically Active Measles Virus Hemagglutinin by Using an Adenovirus Type 5 Helper-Free Vector System," *J. Virol.*, 62(8): 2718-2727 (1988).
Bangari et al., "Comparative Transduction Efficiencies of Human and Nonhuman Adenoviral Vectors in Human, Murine, Bovine, and Porcine Cells in Culture," *Biochemical and Biophysical Research Communications*, 327: 960-966 (2005).
Bangari et al., "Development of Nonhuman Adenoviruses as Vaccine Vectors," *Vaccine*, 24: 849-862 (2006).
Bangari et al., "Porcine Adenoviral Vectors Evade Preexisting Humoral Immunity to Adenovirus and Efficiently Infect Both Human and Murine Cells in Culture," *Virus Research*, 105: 127-136 (2004).
Bett et al., "An Efficient and Flexible System for Construction of Adenovirus Vectors with Insertions or Deletions in Early Regions 1 and 3," *Proc. Natl. Acad. Sci. USA 91*:8802-8806 (1994).
Capua et al., "Vaccination for Avian Influenza in Asia," *Vaccine*, 22: 4137-4138 (2004).
Check, E., "Avian Flu Special: Is This Our Best Shot?" *Nature*, 435: 404-406 (2005).
Chen et al., "Screening of Protective Antigens of Japanese Encephalitis Virus by DNA Immunization: a Comparative Study with Conventional Viral Vaccines," *Journal of Virology*, 73(12): 10137-10145 (1999).
Chen et al., "The Evolution of H5N1 Influenza Viruses in Ducks in Southern China," *Proc. Natl. Acad. Sci. U.S.A.*, 101(28): 10452-10457 (2004).
de Jong et al., "Avian Influenza A (H5N1)," *J. Clin. Virol.*, 35: 2-13 (2006).
Endo et al., "Homotypic and Heterotypic Protection Against Influenza Virus Infection in Mice by Recombinant Vaccina Virus Expressing the Haemagglutinin or Nucleoprotein of Influenza Virus," *J Gen. Virol.*, 72: 699-703 (1991).
Epstein et al., "DNA Vaccine Expressing Conserved Influenza Virus Proteins Protective Against H5N1 Challenge Infection in Mice," *Emerging Infectious Diseases*, 8(8): 796-801 (2002).
Epstein et al., "Protection Against Multiple Influenza A Subtypes by Vaccination with Highly Conserved Nucleoprotein," *Vaccine*, 23: 5404-5410 (2005).

(Continued)

*Primary Examiner* — Bao Li
(74) *Attorney, Agent, or Firm* — Klarquist Sparkman, LLP.

(57) ABSTRACT

The present disclosure provides compositions and methods for eliciting an immune response against avian or pandemic influenza. The compositions include adenovirus vectors comprising avian influenza antigens, recombinant adenovirus and immunogenic compositions comprising such recombinant vectors and adenovirus. Methods for eliciting an immune response against avian or pandemic influenza involving administering such adenovirus vectors or recombinant adenovirus are also provided.

21 Claims, 8 Drawing Sheets

OTHER PUBLICATIONS

Ertl et al., "Novel Vaccine Approaches," *J. Immunol.*, 15: 156(10) 3579-3582 (1996).

Gao et al., "Human Adenovirus Type 35: Nucleotide Sequence and Vector Development," *Gene Therapy*, 10: 1941-1949 (2003).

Gao et al., "Protection of Mice and Poultry from Lethal H5N1 Avian Influenza Virus through Adenovirus-Based Immunization," *J. Viro.*, 80(4): 1959-1964 (2006).

Hien et al., "Avian Influenza A (H5N1) in 10 Patients in Vietnam," *The New England Journal of Medicine*, 350(12): 1179-1188 (2004).

Hoelscher et al., "Development of Adenoviral-Vector-Based Pandemic Influenza Vaccine Against Antigenically Distinct Human H5N1 Strains in Mice," 367: 475-481 (2006).

Kamen et al., "Development and Optimization of an Adenovirus Production Process," The *Journal of Gene Medicine*, 6: S184-S192 (2004).

Katz et al., "Pathogenesis of and Immunity to Avian Influenza A H5 Viruses," *Biomed & Pharmacother*, 54: 178-187 (2000).

Kodihalli et al., "Strategies for Inducing Protection Against Avian Influenza A Virus Subtypes with DNA Vaccines," *Vaccine*, 18: 2592-2599 (2000).

Kodihalli et al., "DNA Vaccine Encoding Hemagglutinin Provides Protective Immunity against H5N1 Influenza Virus Infection in Mice," *J. Virol.* 73:2094-2098 (1999).

Lee et al., "Venezuelan Equine Encephalitis Virus-Vectored Vaccines Protect Mice Against Anthrax Spore Challenge," *Infection and Immunity*, 71(3): 1491-1496 (2003).

Li et al., "Recombinant Influenza A Virus Vaccines for the Pathogenic Human A/hong kong/97 (H5N1) Viruses," *The Journal of Infectious Diseases*, 179(5): 1132-1138 (1999).

Lipatov et al., "Efficacy of H5 Influenza Vaccines Produced by Reverse Genetics in a Lethal Mouse Model," *J. Infect. Dis.*, 191: 1216-1220 (2005).

Lu et al., "A Mouse Model for the Evaluation of Pathogenesis and Immunity to Influenza A (H5N1) Viruses Isolated from Humans," *Journal of Virology*, 73(7): 5903-5911 (1999).

Lunn et al., "Antibody Responses to DNA Vaccination of Horses Using the Influenza Virus Hemagglutinin Gene," *Vaccine*, 17: 2245-2258 (1999).

Moffatt et al., "Circumvention of Vector-Specific Neutralizing Antibody Response by Alternating Use of Human and Non-Human Adenoviruses: Implications in Gene Therapy," *Virology*, 272: 159-167 (2000).

Reddy et al., "Porcine Adenovirus-3 as a Helper-Dependent Expression Vector," *Journal of General Virology*, 80: 2909-2916 (1999).

Romano et al., "Latest Developments in Gene Transfer Technology: Achievements, Perspectives, and Controversies Over Therapeutic Applications," *Stem Cells*, 18: 19-39 (2000).

Sarukhan et al., "Successful Interference with Cellular Immune Response to Immunogenic Proteins Encoded by Recombinant Viral Vectors," *J. Virol.*, 75(1): 269-277 (2001).

Stephenson et al., "Boosting Immunity of Influenza H5N1 with MF59-Adjuvanted H5N3 A/Duck/Singapore/97 Vaccine in a Primed Human Population," *Vaccine*, 21: 1687-1693 (2003).

Stephenson et al., "Confronting the Avian Influenza Threat: Vaccine Development for a Potential Pandemic," *Lancet Infectious Diseases*, 4: 499-509 (2004).

Swayne et al., "Protection Against Diverse Highly Pathogenic H5 Avian Influenza Viruses in Chickens Immunized with a Recombinant Fowlpox Vaccine Containing an H5 Avian Influenza Hemagglutinin Gene Insert," *Vaccine*, 18: 1088-1095 (2000).

Takada et al., "Avirulent Avian Influenza Virus as a Vaccine Strain Against a Potential Human Pandemic," *J. Virol*, 73(10): 8303-8307 (1999).

Tang et al., Recombinant Adenovirus Encoding the HA Gene from Swine H3N2 Influenza Virus Partially Protects Mice from Challenge with Heterologous Virus: A/HK/1/68 (H3N2), *Arch Virol*, 147: 2125-2141 (2002).

Treanor et al., "Safety and Immunology of a Recombinant Hemagglutinin Vaccine for H5 Influenza in Humans," *Vaccine*, 19: 1732-1737 (2001).

Van Kampen et al., "Safety and Immunology of Adenovirus-Vectored Nasal and Epicutaneous Influenza Vaccines in Humans," *Vaccine*, 23: 1029-1036 (2005).

Van Olphen et al., "Characterization of Bovine Adenovirus Type 3 E1 Proteins and Isolation of E1-Expressing Cell Lines," *Virology*, 295: 108-118 (2002).

Wesley et al., "Protection of Weaned Pigs by Vaccination with Human Adenovirus 5 Recombinant Viruses Expressing the Hemagglutinin and the Nucleoprotein of H3N2 Swine Influenza Virus," *Vaccine*, 22: 3427-3434 (2004).

Wood et al., "Preparation of Vaccines Against H5N1 Influenza," *Vaccine*, 20: S84-S87 (2002).

Xiang et al., "A Replication-defective Human Adenovirus Recombinant Serves as a Highly Efficacious Vaccine Carrier," *Virology*, 219(0239): 220-227 (1996).

* cited by examiner

SEQUENCE LISTING

<160> NUMBER OF SEQ ID NOS: 22

<210> SEQ ID NO 1
<211> LENGTH: 20
<212> TYPE: DNA
<213> ORGANISM: artificial sequence
<220> FEATURE:
<223> OTHER INFORMATION: immunostimulatory oligonucleotide

<400> SEQUENCE: 1
tccatgagct tcctgatcct 20

<210> SEQ ID NO 2
<211> LENGTH: 20
<212> TYPE: DNA
<213> ORGANISM: artificial sequence
<220> FEATURE:
<223> OTHER INFORMATION: immunostimulatory oligonucleotide

<400> SEQUENCE: 2
tccatgacgt tcctgacgtt 20

<210> SEQ ID NO 3
<211> LENGTH: 22
<212> TYPE: DNA
<213> ORGANISM: artificial sequence
<220> FEATURE:
<223> OTHER INFORMATION: immunostimulatory oligonucleotide

<400> SEQUENCE: 3
tgactgtgaa cgttcgagat ga 22

<210> SEQ ID NO 4
<211> LENGTH: 2950
<212> TYPE: DNA
<213> ORGANISM: Human adenovirus type 5

<400> SEQUENCE: 4
atgagacata ttatctgcca cggaggtgtt attaccgaag aaatggccgc cagtcttttg 60
gaccagctga tcgaagaggt actggctgat aatcttccac ctcctagcca ttttgaacca 120
cctacccttc acgaactgta tgatttagac gtgacggccc ccgaagatcc caacgaggag 180

```
gcggtttcgc agatttttcc cgactctgta atgttggcgg tgcaggaagg gattgactta    240 ctcactttc cgccggcgcc cggttctccg gagccgcctc acctttcccg gcagcccgag     300
cagccggagc agagagcctt gggtccggtt tctatgccaa accttgtacc ggaggtgatc    360
gatcttacct gccacgaggc tggctttcca cccagtgacg acgaggatga agagggtgag    420
gagtttgtgt tagattatgt ggagcacccc gggcacggtt gcaggtcttg tcattatcac    480
cggaggaata cggggaccc agatattatg tgttcgcttt gctatatgag gacctgtggc     540
atgtttgtct acagtaagtg aaaattatgg gcagtgggtg atagagtggt gggtttggtg    600
tggtaatttt tttttaatt tttacagttt tgtggtttaa agaattttgt attgtgattt     660
ttttaaaagg tcctgtgtct gaacctgagc ctgagcccga gccagaaccg gagcctgcaa    720
gacctacccg ccgtcctaaa atggcgcctg ctatcctgag acgcccgaca tcacctgtgt    780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataaggtg taaacctgtg attgcgtgtg tggttaacgc   1020
ctttgtttgc tgaatgagtt gatgtaagtt taataaaggg tgagataatg tttaacttgc   1080
atggcgtgtt aaatggggcg gggcttaaag ggtatataat gcgccgtggg ctaatcttgg   1140
ttacatctga cctcatggag gcttgggagt gtttggaaga ttttctgct gtgcgtaact    1200 tgctggaaca gagctctaac agtacctctt ggttttggag gttctgtgg ggctcatccc    1260 aggcaaagtt agtctgcaga attaaggagg attacaagtg ggaatttgaa gagcttttga   1320
aatcctgtgg tgagctgttt gattctttga atctgggtca ccaggcgctt ttccaagaga   1380
aggtcatcaa gactttggat ttttccacac cggggcgcgc tgcggctgct gttgctttt    1440 tgagttttat aaaggataaa tggagcgaag aaacccatct gagcgggggg tacctgctgg   1500
attttctggc catgcatctg tggagagcgg ttgtgagaca caagaatcgc ctgctactgt   1560
tgtcttccgt ccgcccggcg ataataccga cggaggagca gcagcagcag caggaggaag   1620
ccaggcggcg gcggcaggag cagagcccat ggaacccgag agccggcctg gaccctcggg   1680
aatgaatgtt gtacaggtgg ctgaactgta tccagaactg agacgcattt tgacaattac   1740
agaggatggg caggggctaa aggggtaaa gagggagcgg ggggcttgtg aggctacaga    1800
ggaggctagg aatctagctt ttagcttaat gaccagacac cgtcctgagt gtattacttt   1860
tcaacagatc aaggataatt gcgctaatga gcttgatctg ctggcgcaga agtattccat   1920
agagcagctg accacttact ggctgcagcc aggggatgat tttgaggagg ctattagggt   1980
atatgcaaag gtggcactta ggccagattg caagtacaag atcagcaaac ttgtaaatat   2040
caggaattgt tgctacattt ctgggaacgg ggccgaggtg gagatagata cggaggatag   2100
ggtggccttt agatgtagca tgataaatat gtggccgggg gtgcttggca tggacggggt   2160
ggttattatg aatgtaaggt ttactggccc caatttagc ggtacggttt tcctggccaa    2220
taccaacctt atcctacacg gtgtaagctt ctatgggttt aacaatacct gtgtggaagc   2280
ctggaccgat gtaagggttc ggggctgtgc cttttactgc tgctggaagg gggtggtgtg   2340
tcgccccaaa agcagggctt caattaagaa atgcctcttt gaaaggtgta ccttgggtat   2400
cctgtctgag ggtaactcca gggtgcgcca caatgtggcc tccgactgtg gttgcttcat   2460
gctagtgaaa agcgtggctg tgattaagca taacatggta tgtggcaact gcgaggacag   2520
ggcctctcag atgctgacct gctcggacgg caactgtcac ctgctgaaga ccattcacgt   2580
```

```
agccagccac tctcgcaagg cctggccagt gtttgagcat aacatactga cccgctgttc    2640
cttgcatttg ggtaacagga ggggggtgtt cctaccttac caatgcaatt tgagtcacac    2700
taagatattg cttgagcccg agagcatgtc caaggtgaac ctgaacgggg tgtttgacat    2760
gaccatgaag atctggaagg tgctgaggta cgatgagacc cgcaccaggt gcagaccctg    2820
cgagtgtggc ggtaaacata ttaggaacca gcctgtgatg ctggatgtga ccgaggagct    2880
gaggcccgat cacttggtgc tggcctgcac ccgcgctgag tttggctcta gcatgaaga     2940 tacagattga                                                           2950

<210> SEQ ID NO 5
<211> LENGTH: 20
<212> TYPE: DNA
<213> ORGANISM: artificial sequence
<220> FEATURE:
<223> OTHER INFORMATION: oligonucleotide primer

<400> SEQUENCE: 5
ccatgaagta cctggtcctc                                                  20

<210> SEQ ID NO 6
<211> LENGTH: 21
<212> TYPE: DNA
<213> ORGANISM: artificial sequence
<220> FEATURE:
<223> OTHER INFORMATION: oligonucleotide primer

<400> SEQUENCE: 6
ccccacctat ttatacccct c                                                21

<210> SEQ ID NO 7
<211> LENGTH: 2507
<212> TYPE: DNA
<213> ORGANISM: Bovine adenovirus type 3

<400> SEQUENCE: 7
atgaagtacc tggtcctcgt tctcaacgac ggcatgagtc gaattgaaaa agctctcctg      60
tgcagcgatg tgaggtgga tttagagtgt catgaggtac ttccccttc tcccgcgcct      120 gtccccgctt ctgtgtcacc cgtgaggagt cctcctcctc tgtctccggt gtttcctccg     180
tctccgccag ccccgcttgt gaatccagag gcgagttcgc tgctgcagca gtatcggaga     240
gagctgttag agaggagcct gctccgaacg gccgaaggtc agcagcgtgc agtgtgtcca     300
tgtgagcggt tgcccgtgga agaggatgag tgtctgaatg ccgtaaattt gctgtttcct     360
gatccctggc taaatgcagc tgaaaatggg ggtgatattt taagtctcc ggctatgtct      420 ccagaaccgt ggatagattt gtctagctac gatagcgatg tagaagaggt gactagtcac     480
ttttttctgg attgccctga gaccccagt cgggagtgtt catcttgtgg gtttcatcag      540
gctcaaagcg gaattccagg cattatgtgc agtttgtgct acatgcgcca aacctaccat     600
tgcatctata gtaagtacat tctgtaaaag aacatcttgg tgatttctag gtattgttta     660
gggattaact gggtggagtg atcttaatcc ggcataacca aatacatgtt ttcacaggtc     720
cagtttctga agaggaaatg tgagtcatgt tgactttggc gcgcaagagg aaatgtgagt     780
catgttgact ttggcgcgcc ctacggtgac tttaaagcaa tttgaggatc acttttttgt     840
tagtcgctat aaagtagtca cggagtcttc atggatcact taagcgttct tttggatttg     900
aagctgcttc gctctatcgt agcgggggct tcaaatcgca ctggagtgtg aagaggcgg      960 ctgtggctgg gacgcctgac tcaactggtc catgatacct gcgtagagaa cgagagcata     1020
```

-continued

```
tttctcaatt ctctgccagg gaatgaagct tttttaaggt tgcttcggag cggctatttt    1080
gaagtgtttg acgtgtttgt ggtgcctgag ctgcatctgg acactccggg tcgagtggtc    1140
gccgctcttg ctctgctggt gttcatcctc aacgatttag acgctaattc tgcttcttca    1200
ggctttgatt caggttttct cgtggaccgt ctctgcgtgc cgctatggct gaaggccagg    1260
gcgttcaaga tcacccagag ctccaggagc acttcgcagc cttcctcgtc gcccgacaag    1320
acgacccaga ctaccagcca gtagacgggg acagcccacc ccgggctagc tggaggagg    1380 ctgaacagag cagcactcgt ttcgagcaca tcagttaccg agacgtggtg gatgacttca    1440
atagatgcca tgatgttttt tatgagaggt acagttttga ggacataaag agctacgagg    1500 cttttgcctga ggacaatttg gagcagctca tagctatgca tgctaaaatc aagctgctgc    1560
ccggtcggga gtatgagttg actcaacctt tgaacataac atcttgcgcc tatgtgctcg    1620
gaaatggggc tactattagg gtaacagggg aagcctcccc ggctattaga gtggggggcca    1680 tggccgtggg tccgtgtgta acaggaatga ctggggtgac ttttgtgaat tgtaggtttg    1740
agagagagtc aacaattagg gggtccctga tacgagcttc aactcacgtg ctgtttcatg    1800
gctgttattt tatgggaatt atgggcactt gtattgaggt ggggcggga gcttacattc    1860 ggggttgtga gtttgtgggc tgttaccggg gaatctgttc tacttctaac agagatatta    1920
aggtgaggca gtgcaacttt gacaaatgct tactgggtat tacttgtaag ggggactatc    1980
gtctttcggg aaatgtgtgt tctgagactt tctgctttgc tcatttagag ggagagggtt    2040
tggttaaaaa caacacagtc aagtccccta gtcgctggac cagcgagtct ggcttttcca    2100
tgataacttg tgcagacggc agggttacgc ctttgggttc cctccacatt gtgggcaacc    2160
gttgtaggcg ttggccaacc atgcagggga atgtgtttat catgtctaaa ctgtatctgg    2220
gcaacagaat agggactgta gccctgcccc agtgtgcttt ctacaagtcc agcatttgtt    2280
tggaggagag ggcgacaaac aagctggtct tggcttgtgc ttttgagaat aatgtactgg    2340
tgtacaaagt gctgagacgg gagagtccct caaccgtgaa aatgtgtgtt tgtgggactt    2400
ctcattatgc aaagcctttg acactggcaa ttatttcttc agatattcgg gctaatcgat    2460
acatgtacac tgtggactca acagagttca cttctgacga ggattaa                 2507
```

<210> SEQ ID NO 8
<211> LENGTH: 25
<212> TYPE: DNA
<213> ORGANISM: artificial sequence
<220> FEATURE:
<223> OTHER INFORMATION: oligonucleotide primer

<400> SEQUENCE: 8

```
ctgatatcat gaagtacctg gcctc                                           25
```

<210> SEQ ID NO 9
<211> LENGTH: 18
<212> TYPE: DNA
<213> ORGANISM: artificial sequence
<220> FEATURE:
<223> OTHER INFORMATION: oligonucleotide primer

<400> SEQUENCE: 9

```
atgcaatggt aggtttgg                                                   18
```

<210> SEQ ID NO 10
<211> LENGTH: 25
<212> TYPE: DNA
<213> ORGANISM: artificial sequence
<220> FEATURE:

```
<223> OTHER INFORMATION: oligonucleotide primer

<400> SEQUENCE: 10
gatatcatgg atcacttaag cgttc                                         25

<210> SEQ ID NO 11
<211> LENGTH: 25
<212> TYPE: DNA
<213> ORGANISM: artificial sequence
<220> FEATURE:
<223> OTHER INFORMATION: oligonucleotide primer

<400> SEQUENCE: 11
gtcgacaact gatgtgctcg aaacg                                         25

<210> SEQ ID NO 12
<211> LENGTH: 24
<212> TYPE: DNA
<213> ORGANISM: artificial sequence
<220> FEATURE:
<223> OTHER INFORMATION: oligonucleotide primer

<400> SEQUENCE: 12
gatatcgttc aagatcaccc agag                                          24

<210> SEQ ID NO 13
<211> LENGTH: 23
<212> TYPE: DNA
<213> ORGANISM: artificial sequence
<220> FEATURE:
<223> OTHER INFORMATION: oligonucleotide primer

<400> SEQUENCE: 13
gtcgaccact tttaatcctg ctc                                           23

<210> SEQ ID NO 14
<211> LENGTH: 27
<212> TYPE: DNA
<213> ORGANISM: artificial sequence
<220> FEATURE:
<223> OTHER INFORMATION: oligonucleotide primer

<400> SEQUENCE: 14
tggatcctcg acatggcgaa cagactt                                       27

<210> SEQ ID NO 15
<211> LENGTH: 29
<212> TYPE: DNA
<213> ORGANISM: artificial sequence
<220> FEATURE:
<223> OTHER INFORMATION: oligonucleotide primer

<400> SEQUENCE: 15
tctcgagtca tcctcagtca tcgtcatcg                                     29

<210> SEQ ID NO 16
<211> LENGTH: 2722
<212> TYPE: DNA
<213> ORGANISM: Porcine adenovirus 3

<400> SEQUENCE: 16
atggcgaaca gacttcacct ggactgggac ggaaacccg aggtggtgcc ggtgctggaa     60
tgggacccgg tggatctgcg cgaccccctct ccgggggatg agggcttctg tgagccgtgc    120
tgggagagtc tggtcgatgg actgccggac gagtggctgg acagtgtgga cgaggtggag    180
```

```
gtgattgtga ctgaggggg tgagtcagag acagtggtg ggagtgccgc tggtgactca     240
ggtggctctc aggggtctt tgagatggac ccccagaag aggggacag taatgaggag      300 gatatcagcg cggtggctgc ggaggtgctg tctgaactgg ctgatgtggt gtttgaggac    360
ccacttgcgc caccctctcc gtttgtgttg gactgccccg aggtacctgg tgtgaactgc    420
cgctcttgtg attaccatcg ctttcactcc aaggacccca atctgaagtg cagtctgtgc    480
tacatgaggg atgcatgcct ttgctgtcta tggtgagtgt ttttggacat ttgtgggatt    540
atgtggaaaa aaaggaaaaa gtgcttgtaa gaaatctcat gtgctatttc ccattttttg    600
tctttttaga agctgtttct ccagcacctc acaggtcggg ttccccggga cttggagacc    660
tgccaggacg caagaggaag tactgctatg actcatgcag cgaacaacct ttggacctgt    720
ctatgaagcg ccccgcgat taatcattaa cctcaataaa cagcatgtga tgatgactga    780
ttgtctgtgt ctctgcctat atatacccctt gtggtttgca gggaagggat gtggtgactg    840
agctattcct cagcatcatc atcgctctgc ttttttctac tgcaggctat ttcttgctag    900
ctcgctgtcc ctttctttt tctgtgggca tggactatca acttctggcc aagcttacta     960
acgtgaacta ccttaggaag gtgatagtac agggtctca gaactgccct tggtggaaaa    1020 agatttttc ggacaggttt atcaaggtag tagcagaggc caggaggcag tacgggcaag    1080
agttgattga gattttttgtg gagggtgaga ggggctttgg tcctgagttc ctgcgggaag    1140 gggactgta cgaagaggcc gttctgaaag agttggattt cagcaccttg gacgcaccg    1200 tagctagtgt ggctctggtc tgcttcattt ttgagaagct tcagaagcac agcgggtgga    1260
ctgacgaggg tattttaagt cttctggtgc cgccactatg ttccctgctg gaggcgcgaa    1320
tgatggcgga gcaggtgcgg caggggctgt gcatcatcag gatgccgagc gcggagcggg    1380
agatgctgtt gcccagtggg tcatccggca gtggcagcgg ggccgggatg cgggaccagg    1440
tggtgcccaa gcgcccgcgg gagcaggaag aggaggagga ggacgaggat gggatggaag    1500
cgagcgggcg caggctcgaa gggccggatc tggtttagat cgccgccggc ccgggggagc    1560
gggtggagag gggagcgggg aggaggcggg ggggtcttcc atggttagct atcagcaggt    1620
gctttctgag tatctggaga gtcctctgga gatgcatgag cgctacagct ttgagcagat    1680
taggccctat atgcttcagc cggggatga tctgggggag atgatagccc agcacgccaa    1740
ggtggagttg cagcccggca cggtgtacga gctgaggcgc ccgatcacca tccgcagcat    1800
gtgttacatc atcgggaacg gggccaagat caagattcgg gggaattaca cggagtacat    1860
caacatagag ccgcgtaacc acatgtgttc cattgcgggc atgtggtcgg tgactatcac    1920
ggatgtggtt tttgatcggg agctaccggc ccggggtggt ctgattttag ccaacacgca    1980
cttcatcctg cacggctgca acttcctggg cttttctggc tcggtaataa cggcgaacgc    2040 cggggggtg gtgcgggat gctacttttt cgcctgctac aaggcgcttg accaccgggg    2100
gcggctgtgg ctgacggtga acgagaacac gtttgaaaag tgtgtgtacg cggtggtctc    2160
tgcggggcgt tgcaggatca agtacaactc ctccctgtcc accttctgct tcttgcacat    2220
gagctatacg ggcaagatag tggggaacag catcatgagc ccttacacgt tcagcgacga    2280 ccccctacgtg gacctggtgt gctgccagag cgggatggtg atgcccctga gcacggtgca    2340
catcgctccc tcgtctcgcc tgccctaccc tgagttccga agaatgtgc tcctccgcag    2400 caccatgttt gtgggcggcc gcctgggcag cttcagcccc agccgctgct cctacagcta    2460
cagctccctg gtggtggacg agcagtccta ccgggctctg agtgtgacct gctgcttcga    2520
tcagacctgt gagatgtaca agctgctgca gtgtacggag gcggacgaga tggagacgga    2580
```

```
                                             -continued tacctctcag cagtacgcct gcctgtgcgg ggacaatcac ccctggccgc aggtgcggca      2640
gatgaaagtg acagacgcgc tgcgggcccc ccggtccctg gtgagctgca actgggggga      2700
gttcagcgat gacgatgact ga                                              2722

<210> SEQ ID NO 17
<211> LENGTH: 22
<212> TYPE: DNA
<213> ORGANISM: artificial sequence
<220> FEATURE:
<223> OTHER INFORMATION: oligonucleotide primer

<400> SEQUENCE: 17
aggtggaggt gattgtgact ga                                              22

<210> SEQ ID NO 18
<211> LENGTH: 22
<212> TYPE: DNA
<213> ORGANISM: artificial sequence
<220> FEATURE:
<223> OTHER INFORMATION: oligonucleotide primer

<400> SEQUENCE: 18
gacgcaagag gaagtactgc ta                                              22

<210> SEQ ID NO 19
<211> LENGTH: 24
<212> TYPE: DNA
<213> ORGANISM: artificial sequence
<220> FEATURE:
<223> OTHER INFORMATION: oligonucleotide primer

<400> SEQUENCE: 19
ctggccaagc ttactaacgt gaac                                            24

<210> SEQ ID NO 20
<211> LENGTH: 22
<212> TYPE: DNA
<213> ORGANISM: artificial sequence
<220> FEATURE:
<223> OTHER INFORMATION: oligonucleotide primer

<400> SEQUENCE: 20
tttaagtctt ctggtgccgc ca                                              22

<210> SEQ ID NO 21
<211> LENGTH: 22
<212> TYPE: DNA
<213> ORGANISM: artificial sequence
<220> FEATURE:
<223> OTHER INFORMATION: oligonucleotide primer

<400> SEQUENCE: 21
atgcatgagc gctacagctt tg                                              22

<210> SEQ ID NO 22
<211> LENGTH: 22
<212> TYPE: DNA
<213> ORGANISM: artificial sequence
<220> FEATURE:
<223> OTHER INFORMATION: oligonucleotide primer

<400> SEQUENCE: 22
ctgagttccg caagaatgtg ct                                              22
```

VACCINE AGAINST PANDEMIC STRAINS OF INFLUENZA VIRUSES

CROSS REFERENCE TO RELATED APPLICATIONS

This application is a continuation of U.S. application Ser. No. 11/911,189, filed Oct. 10, 2007 now abandoned, which is the U.S. National Stage of International Application No. PCT/US2006/013384, filed Apr. 10, 2006, which was published in English under PCT Article 21(2), which in turn claims priority to U.S. Provisional Application No. 60/670,826, filed Apr. 11, 2005, the specification of which is incorporated by reference in its entirety.

ACKNOWLEDGMENT OF GOVERNMENT SUPPORT

Aspects of this disclosure were made with the support of the United States Government pursuant to a grant from the National Institutes of Health. The Government has certain rights in this invention.

FIELD

This application relates to the field of vaccines. More specifically, this application concerns a recombinant vector for the production of vaccines for avian influenza viruses.

BACKGROUND

Pandemic outbreaks of highly virulent avian influenza present a serious risk to human and animal health worldwide. Genetic reassortment between human and avian influenza viruses can result in a virus with a novel hemagglutinin (HA) of avian origin, against which humans lack immunity. In the $20^{th}$ century, the pandemics of 1918, 1957 and 1968 were the result of such antigenic shifts. The recent outbreaks of avian influenza caused by H5N1, H7N7 and H9N2 subtype influenza viruses, and their infection of humans have created a new awareness of the pandemic potential of influenza viruses that circulate in domestic poultry. The estimated economic impact of a pandemic would be up to $165 billion in the United States alone, with as many as 200,000 deaths, 730,000 hospitalizations, 42 outpatient visits, and 50 million additional illnesses.

In the context of prevailing threats of global bioterrorism, individuals deliberately infected with a highly virulent influenza strain could act as difficult-to-detect biological weapons of mass destruction.

To date, three major approaches to developing a safe and effective vaccine against potentially pandemic avian influenza strains have been attempted, none of which is entirely successful (Wood et al., *Vaccine* 20:S84-S87, 2002; Stephenson et al., *The Lancet* 4:499-509, 2004, and references cited therein).

Due to the lethality of these influenza strains in poultry, current vaccine production strategies involving growth of virus in hen's eggs are not feasible. Some approaches have focused on isolating non-pathogenic or attenuated strains of influenza that express the relevant immunogenic antigens of the potentially pandemic influenza strains. For example, naturally occurring, apathogenic strains of influenza with the H5 subtype antigen virus have been evaluated as vaccine candidates. In general, these viruses have proved difficult to grow using conventional technology, and protection is dependent on the ability of antibodies raised against the apathogenic vaccine strain to cross-react with the virulent strain of virus (Takada et al., *J. Virol.* 73:8303-8307, 1999; Wood et al., *Vaccine* 18:579-80, 2000). A reverse genetics approach has been employed to delete a stretch of basic amino acids at the cleavage site of the HA antigen of a pathogenic H5N1 virus (A/HK/97) to develop a candidate vaccine (Li et al., *J. Infect. Dis.* 179:1132-1138, 1999).

Another approach has been to utilize recombinant HA ("H5") produced in a baculovirus expression system. However, high doses of purified protein and the use of adjuvants are required to achieve a satisfactory immune response. (Treanor et al. *Vaccine* 19:1732-1737, 2001).

There remains a need to develop vaccines that are protective against infection by avian influenza strains in both human and non-human populations, and which can be efficiently produced and administered without reliance on viral growth in hen's eggs. The present disclosure addresses this need, and provides novel compositions and methods useful for preventing infection by avian and pandemic influenza strains.

SUMMARY

The present disclosure relates to methods for eliciting a protective immune response against potentially pandemic strains of influenza, and to compositions, including nucleic acid vectors and non-infectious viruses useful in the methods disclosed herein.

One aspect of the disclosure relates to recombinant nucleic acids. The recombinant nucleic acids described herein include adenovirus vectors. The adenovirus vectors, including human and non-human adenovirus vectors, contain polynucleotide sequences that encode one or more polypeptides that correspond to antigens of avian influenza strains.

In another aspect, the disclosure provides a recombinant adenovirus, for example, a replication defective human or non-human adenovirus that expresses one or more avian influenza antigen.

Pharmaceutical compositions, including vaccine compositions, are disclosed that contain the adenovirus vectors and/or the recombinant adenoviruses disclosed herein.

Another feature of the disclosure relates to methods of producing an immune response against avian and/or pandemic strains of influenza. In the methods disclosed herein, immunogenic compositions based on adenovirus vectors encoding and/or recombinant adenoviruses expressing at least one antigen of an avian influenza strain are administered to a subject prior to or following exposure to an avian or pandemic strain of influenza.

The foregoing and other objects, features, and advantages of the invention will become more apparent from the following detailed description, which proceeds with reference to the accompanying figures.

BRIEF DESCRIPTION OF THE SEQUENCE LISTING

Figure 1:
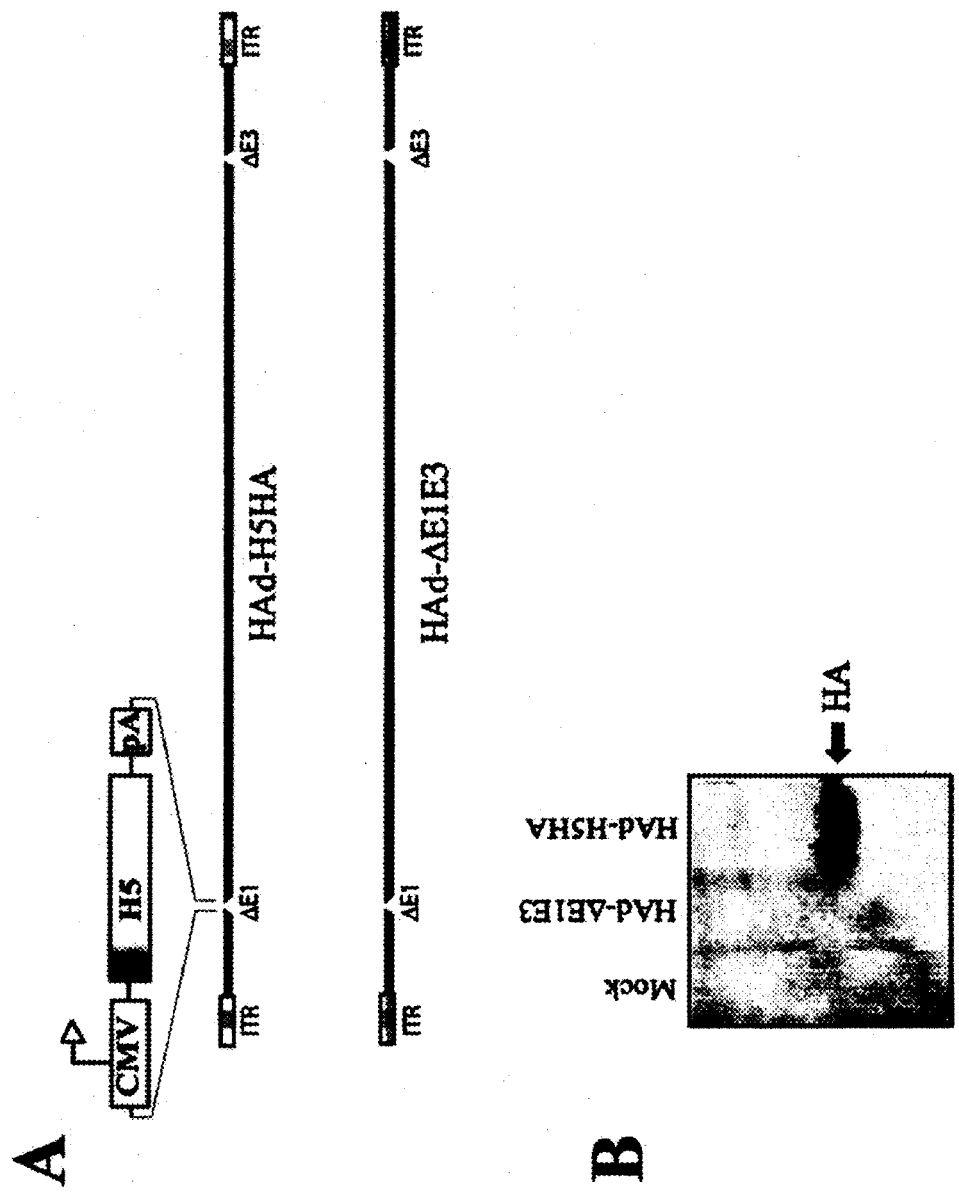
FIG. 1A schematically illustrates the HAd5-H5HA vector. The Cre recombinase-mediated site-specific recombination system was used to generate a HAd5 vector expressing HA of avian influenza virus (H5N1) A/HK/156/97. The HA gene under the control of the CMV promoter was inserted at the StuI site in a shuttle vector (pDC311—a plasmid containing the left end of HAd5 (4 kb) with 3.1 kb E1 deletion, a loxP site for site specific recombination in the presence of Cre recombinase and an intact packaging signal to produce pDC311-H5. 293Cre cells (293 cells expressing Cre recombinase) were cotransfected with pDC311-H5HA and pBHGloxΔE1, 3Cre (plasmid containing almost the entire HAd5 genome except the packaging signal, E1 and E3 deletions, a loxP site for site specific recombination in the presence of Cre recombinase) to generate HAd-H5HA vector.
FIG. 1B is a western blot illustrating expression of hemagglutinin (HA) encoded by the HAd5-H5HA vector. HAd-H5HA efficiently expressed HA in infected cells. Structure of the H5-HA gene cassette in the HAd-H5HA vector (A) and H5HA expression in cells infected with HAd-H5 HA vector (B). 293Cre cells were mock-infected or infected with HAd-ΔE1E3 or HAd-H5HA. At 24 h post-infection cells were harvested and cell extracts were prepared. Cell extracts were analyzed by Western blot using a rabbit H5HA-specific sera generated by immunizing rabbits with a DNA vector encoding H5HA.

SEQ ID NO:1 (5'-tccatgagcttcctgatcct-3') is an immunostimulatory oligonucleotide.

SEQ ID NO:2 (5'-tccatgacgttectgacgtt-3') is an immunostimulatory oligonucleotide.

SEQ ID NO:3 (5'-tgactgtgaacgttcgagatga-3)' is an immunostimulatory oligonucleotide.

SEQ ID NO:4 is the nucleotide sequence of HAd5 E1.

SEQ ID NOs:5 and 6 are oligonucleotide primers for the amplification of bovine adenovirus E1.

SEQ ID NO:7 is the nucleotide sequence of BAd3 E1.

SEQ ID NOs:8-13 are oligonucleotide primers for detection of BAd3 E1 transcripts.

SEQ ID NOs:14 and 15 are oligonucleotide primers for the amplification of porcine adenovirus E1.

SEQ ID NO:16 is the nucleotide sequence of PAd3 E1.

SEQ ID NOs:17-22 are oligonucleotide primers for the detection of PAd3 E1 transcripts.

DETAILED DESCRIPTION

Introduction

Influenza viruses are enveloped negative-sense viruses belonging to the Orthomyxoviridae family. Influenza viruses are classified on the basis of their core proteins into three distinct types: A, B, and C. Within these broad classifications, subtypes are further divided based on the characterization of two antigenic surface proteins hemagglutinin (HA) and neuraminidase (NA). While B and C type influenza viruses are largely restricted to humans, influenza A viruses are pathogens of a wide variety of species including humans, non-human mammals, and birds. Periodically, non-human strains, particularly of avian influenza, have infected human populations, in some cases causing severe disease with high mortality. Recombination between such avian strains and human strains in coinfected individuals has given rise to recombinant influenza viruses to which immunity is lacking in the human population, resulting in influenza pandemics. Three such pandemics occurred during the twentieth century, in 1918, 1957, and 1968, resulting in numerous deaths worldwide.

Highly pathogenic avian influenza H5N1 viruses have become endemic in domestic poultry in Southeast Asia. Since early 2004, human infections with H5N1 viruses have been reported in the region with increasing frequency and high mortality rates. Highly pathogenic H5N1 influenza viruses were first recognized to cause respiratory disease in humans in 1997, when 18 documented cases, including 6 deaths, occurred following outbreaks of influenza in poultry farms and markets in Hong Kong. Two additional human H5N1 infections were identified in a family in Hong Kong in 2003. Since then, H5N1 viruses have spread to 9 Asian countries, and recently have expanded their geographical distribution to several countries in Eastern Europe. Over 120 laboratory confirmed cases of human infection with a fatality rate of greater than 50% have been reported to the World Health Organization since January 2004. To date, the majority of human H5N1 virus infections have been due to direct transmission of the virus from infected poultry, although exceptional cases of human-to-human transmission have been reported. Genetic reassortment between a human and avian influenza virus and/or mutations in the avian H5N1 virus genome may result in the generation of a novel influenza virus of the H5 subtype that may initiate a pandemic if it has acquired the ability to undergo sustained transmission in an immunologically naïve human population. Therefore, effective vaccines against highly pathogenic H5N1 and other avian influenza strains are urgently needed.

Vaccines developed and evaluated in response to the 1997 outbreak of H5N1 influenza were only modestly immunogenic in humans, and the H5N1 viruses isolated from humans in 2004 were genetically and antigenically distinct from those isolated previously in 1997 and 2003, necessitating the development of new vaccine candidates because the elicited immune response was not protective against antigenically distinct viral strains.

Non-pathogenic avian influenza viruses, either produced from naturally occurring apathogenic strains that share an HA subtype with a pathogenic strain, or that have been engineered to be apathogenic by deletion of a spontaneous protein cleavage site have thus far been produced only in hen's eggs. In the event of a world-wide pandemic, infection of domestic fowl is likely to be widespread requiring the killing of chickens and resulting in a shortage of eggs to be used for vaccine production. Recombinant HA vaccines have been evaluated, but require potentially detrimental adjuvants for efficient protection. Thus, diversification of vaccine manufacturing substrates including cell-based and/or recombinant DNA technologies is desirable to enhance vaccine production capacity in a pandemic situation. Furthermore, recombinant DNA technologies are advantageous in accelerating vaccine availability, as cloning and expression of one or more viral genes can begin as soon as the viral sequence is known.

The present disclosure provides novel compositions and methods for producing influenza vaccines and vaccinating human, non-human mammals and avian populations against avian and/or pandemic strains of influenza virus and overcoming the poor immunogenicity and manufacturing drawbacks of currently available influenza vaccines, which have been adapted to elicit an immune response against avian strains of influenza. The compositions and methods described herein are based on adenovirus vectors that express one or more immunogenic avian influenza antigen, optionally in combination with internal proteins that further enhance the immune response, reduce morbidity and facilitate recovery following exposure or infection by avian or pandemic influenza strains. This disclosure provides the first evidence that human and non-human adenoviruses are effective vectors for eliciting an immune response against avian (and potentially pandemic) influenza strains. Additionally, the compositions and methods described herein offer several benefits over strategies that have previously been evaluated as vaccines for potentially pandemic strains of avian influenza virus. For example, the adenovirus vectors and adenovirus described herein can readily be grown in tissue culture, and purified at a scale suitable for commercial manufacture. Furthermore, the immune response elicited is robust and long lasting, and depending on the combination of antigens, involves both neutralizing antibody production and T cell responses, and is protective against antigenically distinct strains of influenza.

Description of Exemplary Embodiments

One aspect of the present disclosure relates to recombinant adenovirus vectors that include polynucleotide sequences that encode one or more influenza antigens. In particular, the adenovirus vectors described herein include a polynucleotide sequence that encodes at least one antigen of an avian influenza strain (an "avian influenza antigen"). For example, the adenovirus vector can encode one or more avian hemagglutinin ("HA") antigens. The vector can include a sequence that encodes a single HA of an avian influenza strain, such as an H5 subtype strain, an H7 subtype strain or an H9 subtype strain, e.g., selected from H5N1, H7N7 or H9N2 strains prevalent in recent outbreaks of avian influenza. Alternatively, the vector can encode a plurality (more than one) of avian HA antigens. In this case, the HA antigens encoded can be variants of one subtype (for example, variants of H5 HA, or variants of H7 HA, or variants of H9 HA) or the HA antigens can be HA antigens of different subtypes (that is, a combination of H5, H7 and/or H9, e.g., H5 and H7, H5 and H9, H7 and H9, or H5, H7 and H9, including one or more than one HA antigen of any subtype in combination with one or more than one HA antigen of any other subtype).

The recombinant adenovirus vector can also include a polynucleotide sequence that encodes an avian influenza neuraminidase ("NA") antigen. The NA antigen can be encoded by the vector alone, or in combination with an avian HA antigen. When a vector includes a polynucleotide sequence that encodes both an avian HA antigen and an avian NA antigen, the HA and NA antigens can be of the same strain of influenza, or can be selected from different avian strains of influenza. For example, recent outbreaks of avian influenza in human populations in Asia have been caused by H5N1, H7N7 and H9N2 strains of influenza A. An adenovirus vector can encode, e.g., an N1 subtype NA, an N7 subtype NA, or an N2 subtype of NA. Alternatively, the vector can encode a different NA subtype, such as N3 (e.g., corresponding to an apathogenic H5N3 strain avian influenza virus). One of skill in the art will appreciate that any avian HA subtype (most commonly, H5, H7 or H9) can be combined with any of 9 NA subtypes in an adenovirus vector. As described above with respect to HA antigens, an adenovirus vector can encode a plurality of NA antigens, which can be variants of a single NA subtype or representative of different NA subtypes.

As indicated above, the adenovirus vectors can encode a plurality of influenza antigens. The plurality of influenza antigens can encode two or more avian influenza antigens, such as multiple avian HA antigens, multiple avian NA antigens, or a combination of avian HA antigens and NA antigens. Alternatively, the vectors can encode one or more avian influenza antigens in combination with one or more internal proteins of avian or non-avian influenza strains. In the case of an avian influenza internal protein, the internal protein can be selected from the same or a different strain of avian influenza. The encoded internal protein can also be selected from a non-avian strain of influenza, such as a human strain of influenza (typically, influenza A). For example, the internal protein or proteins can be selected from a H1N1, H2N2 or H3N2 influenza strain. Any of the internal proteins (M1, M2, NP, PB1, PB2, NS1, and NS2) can be encoded by the adenovirus vector. A combination of internal proteins can also be encoded by the vector. For example, the vector can encode an M protein (one or more of M1 and/or M2), an NP protein or both an M and an NP protein.

Human and non-human adenovirus vectors are well-known in the art, and both can be constructed to include one or more of the influenza antigens described above. Human adenovirus vectors include human adenovirus serotype 5 ("HAd5") vectors. Alternatively, the adenovirus vectors are non-human, such as porcine or bovine, adenovirus vectors (for example, BAd3 and PAd3 vectors). Typically, the adenovirus vector is a replication defective adenovirus that is incapable of multiple cycles of transcription and translation of the inserted genes in human or animal cells. The replication defective adenovirus vectors can have mutations in one or more gene (or region) involved in replication, including one or more of an E1 region gene, an E3 region gene, an E2 region gene, and/or an E4 region gene. For example, a replication defective adenovirus vector can have a deletion or mutation in an E1 region gene (e.g., E1A), an E3 region gene, an E2 region gene, an E4 region gene, or a combination thereof.

Thus, in one exemplary embodiment, the adenovirus vector is a replication defective human adenovirus vector that includes a polynucleotide sequence that encodes an avian influenza HA antigen, an avian influenza NA antigen, or both an avian HA antigen and an avian NA antigen. Optionally, the adenovirus vector encodes a plurality of avian HA antigens, which are variants of a single HA subtype or are different HA subtypes. In certain embodiments, the adenovirus vector also encodes at least one influenza internal protein, such as an M1 protein, an M2 protein, an NP protein or a combination of M and NP proteins.

In another embodiment, the adenovirus vector is a replication defective non-human adenovirus vector, such as a porcine or bovine adenovirus vector, that includes a polynucleotide sequence that encodes an avian influenza HA antigen, an avian influenza NA antigen, or both an avian HA antigen and an avian NA antigen. Optionally, the adenovirus vector encodes a plurality of avian HA antigens, which are variants of a single HA subtype or are different HA subtypes. In certain embodiments, the adenovirus vector also encodes at least one influenza internal protein, such as an M1, M2 protein, an NP protein or any combination thereof.

Another aspect of the disclosure relates to a recombinant adenovirus that expresses (includes) at least one antigen of an avian influenza strain. Commonly, the adenovirus expresses an avian HA antigen and/or an avian NA antigen. Thus, the adenovirus can include an avian HA antigen, e.g., an H5 HA antigen, an H7 HA antigen, and/or an H9 HA antigen. Similarly, the adenovirus can include an avian NA antigen, e.g., an H1 NA antigen, an H7 NA antigen, and/or an H2 NA antigen. In some instances, the adenovirus expresses a plurality of avian influenza antigens, such as a plurality of avian HA antigens or a plurality of avian NA antigens or a combination of avian HA and NA antigens. For example, the adenovirus can express two or more variants of a single HA (or NA) subtype. Alternatively, the adenovirus can express two or more HA (or NA) antigens of different subtypes. In some cases, the adenovirus expresses at least one influenza internal protein, such as an M1, M2 and/or NP protein. Where an adenovirus expresses a plurality of influenza antigens, the multiple antigens can be of the same strain or subtype, or a different strains or subtypes.

The recombinant adenovirus can be either a human adenovirus or a non-human adenovirus, such as a porcine or bovine adenovirus. Generally, the adenovirus is a replication defective human or non-human adenovirus. For example, the replication defective adenovirus can have a mutation (e.g., a deletion, addition or substitution) in an E1 region gene, an E3 region gene, an E2 region gene and/or an E4 region gene.

Such adenovirus vectors and adenovirus are useful for a variety of purposes. For example, such adenovirus and adenovirus vectors are useful for producing recombinant avian (and other) influenza antigens in vitro and in vivo (including in ovo). Accordingly, methods for producing recombinant avian influenza antigens are a feature of this disclosure. For example, recombinant avian influenza antigens can be produced by replicating adenovirus that include at least one heterologous polynucleotide sequence that encodes an avian influenza virus antigen. In some embodiments, the adenovirus includes sequences that encode two or more avian influenza virus antigens, or at least one avian influenza virus antigen and a non-avian influenza virus antigen. For example, the avian influenza antigen can be an HA antigen or an NA antigen, such as an HA or NA antigen selected from an H5, an H7 or an H9 strain of influenza. In certain embodiments, the adenovirus contain polynucleotide sequences that encode a plurality of influenza antigens.

In certain embodiments, adenovirus expressing recombinant avian influenza virus antigens are produced by introducing a replication defective adenovirus vector into a cell capable of supporting replication of the replication defective vector. Such cells typically include at least one heterologous nucleic acid that provides a complementary replication function, such as a heterologous nucleic acid that encodes one or more E proteins that are deleted from the replication defective adenovirus vector. In certain embodiments, the cells that are capable of supporting growth of the replication defective adenovirus vector are capable of supporting growth of different strains of adenovirus with different species tropism. Optionally, the recombinant avian influenza virus antigen is isolated, and for example, used to produce immunogenic compositions, such as vaccines.

Another aspect of the disclosure relates to cell lines that support the replication of multiple strains of replication defective adenovirus having different tropisms. Such multifunctional cell lines include heterologous nucleic acids that encode multiple E proteins of different strains of adenovirus. In exemplary embodiments the cell lines include one or more heterologous nucleic acids that include at least two distinct polynucleotide sequences, one of which encodes at least one E protein of a first adenovirus strain and the other of which encodes at least one E protein of a different adenovirus strain. The E proteins are selected to complement those deleted from recombinant adenovirus vectors that are to be grown in the cell lines. Thus, in some embodiment, where the cells are intended to support growth of replication defective adenovirus lacking one or more E1 proteins, the polynucleotide sequence encodes the corresponding E1 protein(s). Similarly, where the cells are intended to support growth of replication defective adenovirus lacking one or more E3 proteins, the polynucleotide sequence encodes the corresponding E3 protein(s). Typically, the cells include nucleic acids that encode E proteins of strains of adenovirus with different species tropism so that the cells optimally support growth of multiple strains of adenovirus with different species tropisms, such as a human adenovirus E gene (or fragment thereof) and a non-human E gene (or fragment thereof). In specific examples, the polynucleotide sequences encode human and either bovine or porcine E proteins.

The adenovirus vectors and recombinant adenoviruses disclosed herein are useful in the context of immunogenic compositions, including vaccines. Such immunogenic compositions can include an adenovirus vector with a polynucleotide sequence that encodes at least one avian influenza antigen as previously discussed. The immunogenic compositions can also include recombinant adenoviruses that express at least one avian influenza antigen as discussed above. The immunogenic compositions include, in addition to the adenovirus vectors and/or adenoviruses, a pharmaceutically acceptable carrier or excipient. Thus, the immunogenic compositions can include any of the adenovirus vectors and/or adenoviruses encoding or expressing avian influenza antigens as disclosed herein. Optionally, the immunogenic compositions include an adjuvant, immunostimulatory molecule, miroparticle, or nanoparticile.

The present disclosure also provides methods for eliciting or producing an immune response against an avian or pandemic (or potentially pandemic) strain of influenza. The methods disclosed herein involve administering at least one adenovirus or adenovirus vector that expresses (or encodes) an avian influenza antigen to a subject. Typically, the adenovirus or adenovirus vector is administered to the subject prior to exposure to at least one strain of avian influenza or pandemic influenza. That is, typically, the adenovirus or adenovirus vector expressing the avian influenza antigen is administered prophylactically, e.g., as a vaccine.

Administration of the recombinant adenoviruses and adenovirus vectors can elicit an immune response that protects the subject from serious disease or death due to infection by one or more avian or pandemic strains of influenza. In some cases, the immune response protects against disease caused by more than one strain of influenza, such as multiple strains of avian influenza. Typically, the immune response includes neutralizing antibodies that bind to at least one avian influenza antigen, and can, in some cases, cross-react with multiple strains of avian influenza. For example, administration of an adenovirus or adenovirus vector that expresses an avian influenza HA antigen can elicit neutralizing antibodies against the subtype of HA that protect (or partially protect) against infection with influenza of the corresponding HA subtype. Similarly, administration of an adenovirus or adenovirus vector that expresses an avian NA antigen can elicit an antibody response against the subtype of NA.

In some cases, an adenovirus or adenovirus vector is administered that expresses (or encodes) two or more avian HA and/or NA antigens. Alternatively, multiple adenovirus or adenovirus vectors, each of which includes a single avian influenza antigen, are administered. Whether administered in a single virus or vector, or in multiple viruses or vectors, the antigens, e.g., the HA antigens, can be variants of the same antigen subtype or can be antigens of different influenza subtypes. Optionally, the one (or several) adenoviruses or vectors results in the expression of an influenza structural or nonstructural protein, such as an M1, M2, NP, or NS1 protein. As is the case for the HA and NA antigens, the internal proteins can be included within one or more than one adenovirus or vector. Inclusion of one or more internal protein antigens is useful in augmenting the immune response generated by a vaccine by enhancing the production of influenza specific T cells. Thus, an immune response elicited by the compositions described herein can include a T cell response. Generally, the T cell response is specific for an epitope of the influenza internal protein that is conserved among a plurality of influenza strains, such as multiple strains of the same or different subtype of influenza.

For example, in one embodiment, a replication defective adenovirus that expresses a single avian HA antigen, such as an H5 HA antigen, an H7 HA antigen, or an H9 antigen, is administered. In another embodiment, an adenovirus that expresses two or more avian HA antigens is administered. In another embodiment, an adenovirus that expresses at least one avian HA antigen and at least one avian NA antigen is administered. In another embodiment, the adenovirus expresses at least one avian HA antigen, at least one avian NA antigen, and one or more influenza internal proteins (such as the M1, M2 and/or NP proteins) of an avian or non-avian strain of influenza. An exemplary embodiment of such an adenovirus is an adenovirus that expresses an H5 avian HA, an N1 avian NA, and human M (M1 and/or M2) and/or NP proteins. Numerous other examples can be determined by those of ordinary skill in the art based on the strain or strains against which an immune response is desired.

In other embodiments, a plurality of different human or nonhuman adenoviruses are administered, each of which includes one or more influenza antigens. For example, multiple adenoviruses can be administered at the same or different times (that is, in one or more immunogenic compositions delivered simultaneously or sequentially). In some cases, multiple adenoviruses are administered in a "cocktail." When administered in a cocktail each adenovirus can express a single influenza antigen, or some or all of the adenoviruses can express multiple influenza antigens. For example, in one favorable cocktail an adenovirus that expresses an H5 avian HA antigen is administered along with an adenovirus that expresses an M2 protein. In another example, an adenovirus that expresses an H5 avian HA antigen and an N1 avian NA antigen is administered in combination with a human influenza M2 and/or NP protein. In another exemplary embodiment, a first adenovirus that expresses a plurality of avian HA antigens (such as variants of a single HA subtype, or corresponding to different HA subtypes) is administered along with a second adenovirus that expresses an avian or human M2 and/or NP protein. Numerous other combinations can be determined by those of ordinary skill in the art.

In other embodiments, adenovirus vectors rather than recombinant adenoviruses are administered to the subject in the form of nucleic acid (e.g., DNA) vaccines.

Optionally, the adenovirus or adenovirus vector is administered to the subject in an immunogenic composition that includes, in addition to a pharmaceutically acceptable carrier or excipient, at least one additional immunostimulatory component. Such immunostimulatory components include adjuvants, such as MF 59 and aluminum adjuvants. Alternatively, naturally occurring or synthetic immunostimulatory compositions that bind to and stimulate receptors involved in innate immunity can be administered along with the adenoviruses and/or adenovirus vectors. For example, agents that stimulate certain Toll-like receptors (such as TLR7, TLR8 and TLR9) can be administered in combination with the adenovirus recombinants and/or adenovirus vectors that express influenza antigens. In some embodiments, the adenovirus or vector is administered in combination with immunostimulatory CpG oligonucleotides. In other embodiments, the adenovirus or vector is administered in combination with additional adenovirus vectors that express a Toll-like receptor and a ligand that results in activation of the receptor, respectively.

The immunogenic compositions described herein can be administered to human or non-human (for example, cats, dogs, pigs, birds) subjects to elicit an influenza specific immune response. For example, if the subject is a human subject, a human, bovine or porcine adenovirus recombinant (or adenovirus vector) including one or more avian influenza antigens can be administered to elicit an immune response. Additionally, the compositions and methods described herein can be utilized to elicit influenza specific immune responses in avian subjects, including domesticated fowl, such as chickens, ducks, guinea fowl, turkeys, geese and the like. Additionally, the compositions and methods described herein can be utilized to elicit influenza specific immune responses in non-human subjects, including cats, dogs, horses, non-human primates, and other domestic and wild mammals.

A variety of routes of administration are suitable for administering the immunogenic compositions described herein. Such methods include intranasal, oral, ocular, intravenous, intramuscular, transdermal, intradermal and subcutaneous delivery of the adenoviruses and/or adenovirus vectors. In specific embodiments, the immunogenic compositions are administered to domesticated fowl, in their drinking water, by spray or controlled droplet or in ovo prior to hatching.

Additional technical details are provided under the specific topic headings below.

Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin *exempli gratia*, and is used herein to indicate a non-limiting example. Thus, the abbreviation "e.g." is synonymous with the term "for example."

In order to facilitate review of the various embodiments of this disclosure, the following explanations of specific terms are provided:

Adjuvant: A vehicle used to enhance antigenicity; such as a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages).

Antigen: A compound, composition, or substance that can stimulate the production of antibodies or a T cell response in an animal, including compositions that are injected, absorbed or otherwise introduced into an animal. The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. In one embodiment, T cells respond to the epitope when the epitope is presented in conjunction with an MHC molecule. Epitopes can be formed both from contiguous amino acids or noncontiguous amino acids juxtaposed by tertiary folding of an antigenic polypeptide. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and multi-dimensional nuclear magnetic resonance spectroscopy.

An influenza antigen can be a polymorphic hemagglutinin (HA) or neuraminidase (NA) antigen selected from an influenza strain to which an immune response is desirable or a related strain that shares antigenic epitopes. An influenza antigen can also be an influenza internal protein, such as a PB1, PB2, PA, M1, M2, NP, NS1 or NS2 protein. An avian influenza antigen is an influenza antigen of an avian influenza strain. A variant of an influenza antigen can be a naturally occurring variant or an engineered variant. As used herein, the term "variant" refers to a protein (e.g., an antigen) with one or more amino acid alterations, such as deletions, additions or substitutions, relative to a reference protein or with respect to another variant.

Antibody: Immunoglobulin molecules and immunologically active portions of immunoglobulin molecules, that is, molecules that contain an antigen binding site that specifically binds (immunoreacts with) an antigen. A naturally occurring antibody (e.g., IgG, IgM, IgD) includes four polypeptide chains, two heavy (H) chains and two light (L) chains interconnected by disulfide bonds. The phrase "antibody response" refers to an immunological response against an antigen involving the secretion of antibodies specific for the antigen. An antibody response is a B cell mediated immune response initiated through the interaction of an antigen (or epitope) with a B cell receptor (membrane bound IgD) on the surface of a B cell. Following binding of the stimulation of the B cell receptor by its cognate antigen, the B cell differentiates into a plasma cell that secretes antigen specific immunoglobulin to produce an antibody response. "Neutralizing antibodies" are antibodies that bind to an epitope on a virus inhibiting infection and/or replication as measured, e.g., in a plaque neutralization assay.

Animal: Living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

cDNA (complementary DNA): A piece of DNA lacking internal, non-coding segments (introns) and regulatory sequences that determine transcription. cDNA is typically synthesized in the laboratory by reverse transcription from messenger RNA extracted from cells. In the context of preparing adenovirus vectors including polynucleotide sequences that encode influenza antigen, a cDNA can be prepared, for example by reverse transcription or amplification (e.g., by the polymerase chain reaction, PCR) from a negative stranded influenza RNA genome (or genome segment).

Host cells: Cells in which a polynucleotide, for example, a polynucleotide vector or a viral vector, can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Thus, the adenovirus vectors described herein can be introduced into host cells where their polynucleotide sequences (including those encoding influenza antigen(s)) can be expressed, e.g., to produce recombinant adenoviruses and/or influenza antigens.

Immune response: A response of a cell of the immune system, such as a B cell, T cell, or monocyte, to a stimulus. In some cases, the response is specific for a particular antigen (that is, an "antigen-specific response"). In some cases, an immune response is a T cell response, such as a CD4+ response or a CD8+ response. Alternatively, the response is a B cell response, and results in the production of specific antibodies. A "protective immune response" is an immune response that inhibits a detrimental function or activity of a pathogenic influenza virus, reduces infection by a pathogenic influenza virus, or decreases symptoms (including death) that result from infection by the pathogenic organism. A protective immune response can be measured, for example, by the inhibition of viral replication or plaque formation in a plaque reduction assay or ELISA-neutralization assay (NELISA), or by measuring resistance to viral challenge in vivo. A cell-mediated immune response can be measured by various immunological assays, e.g., ELISpot, tetramer-labelling, cytotoxicity assay.

Immunogenic composition: A composition comprising at least one epitope of an influenza virus (or other pathogenic organism), that induces a measurable CTL response, or induces a measurable B cell response (for example, production of antibodies that specifically bind the epitope). It further refers to isolated nucleic acids encoding an immunogenic epitope of an influenza virus (or other pathogen) that can be used to express the epitope (and thus be used to elicit an immune response against this polypeptide or a related polypeptide expressed by the pathogen). For in vitro use, the immunogenic composition can consist of the isolated nucleic acid, protein or peptide. For in vivo use, the immunogenic composition will typically include the nucleic acid or virus that expresses the immunogenic epitope in pharmaceutically acceptable carriers or excipients, and/or other agents, for example, adjuvants. An immunogenic polypeptide (such as an influenza antigen), or nucleic acid encoding the polypeptide, can be readily tested for its ability to induce a CTL or antibody response by art-recognized assays.

Internal Protein: The internal proteins of influenza include all of the structural and nonstructural proteins encoded by the influenza genome, with the exception of the two surface antigens hemagglutinin (HA) and neuraminidase (NA). The internal proteins of influenza A are encoded by six genomic RNA segments and include three polymerase components designated PB1, PB2 and PA; the nucleocapsid protein (NP); the matrix protein (M1); the membrane channel protein (M2); and two nonstructural proteins: NS1 and NS2.

Isolated: An "isolated" biological component (such as a nucleic acid or protein or organelle) has been substantially separated or purified away from other biological components in the cell of the organism in which the component naturally occurs, for example, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA or RNA.

Polypeptide: Any chain of amino acids, regardless of length or post-translational modification (for example, glycosylation or phosphorylation), such as a protein or a fragment or subsequence of a protein. The term "peptide" is typically used to refer to a chain of amino acids of between 3 and 30 amino acids in length. For example an immunologically relevant peptide may be between about 7 and about 25 amino acids in length, e.g., between about 8 and about 10 amino acids.

Preventing or treating a disease: Inhibiting infection by an influenza virus refers to inhibiting the full development of disease caused by exposure to a pathogenic influenza virus. For example, inhibiting an influenza infection refers to lessening symptoms resulting from infection by the virus, such as preventing the development of symptoms in a person who is known to have been exposed to the virus, or to lessening virus number or infectivity of a virus in a subject exposed to the virus. "Treatment" refers to a therapeutic or prophylactic intervention that ameliorates or prevents a sign or symptom of a disease or pathological condition related to infection of a subject with a virus.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the cytomegalovirus immediate early gene promoter, the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term "purified" (e.g., with respect to an adenovirus vector or recombinant adenovirus) does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the specified component represents at least 50% (such as, but not limited to, 70%, 80%, 90%, 95%, 98% or 99%) of the total preparation by weight or volume.

Recombinant: A recombinant nucleic acid is one that has a sequence that is not naturally occurring or has a sequence that is made by an artificial combination of two otherwise separated segments of sequence, for example, a polynucleotide encoding a fusion protein. This artificial combination is often accomplished by chemical synthesis or, more commonly, by the artificial manipulation of isolated segments of nucleic acids, e.g., by genetic engineering techniques.

Subject: Living multi-cellular vertebrate organisms, a category that includes both human and veterinary subjects, including human and non-human mammals and birds.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as CD4. These cells, also known as helper T cells, help orchestrate the immune response, including antibody responses as well as killer T cell responses. CD8$^+$ T cells carry the CD8 marker, and include T cells with cytotoxic or "killer" effector function.

Transduced or Transfected: A transduced cell is a cell into which a nucleic acid molecule has been introduced by molecular biology techniques. As used herein, the term introduction or transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A vaccine is a pharmaceutical composition that elicits a prophylactic or therapeutic immune response in a subject. In some cases, the immune response is a protective immune response. Typically, a vaccine elicits an antigen-specific immune response to an antigen of a pathogen. In the context of this disclosure, the vaccines elicit an immune response against avian (or pandemic) influenza. The vaccines described herein include adenovirus vectors or recombinant adenoviruses.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. The term vector includes plasmids, linear nucleic acid molecules, and as described throughout adenovirus vectors and adenoviruses. The term adenovirus vector is utilized herein to refer to nucleic acids including one or more components of an adenovirus that replicate to generate (e.g., infectious) viral particles in host cells. An adenovirus includes nucleic acids that encode at least a portion of the assembled virus. Thus, in many circumstances, the terms can be used interchangeably. Accordingly, as used herein the terms are used with specificity to facilitate understanding and without the intent to limit the embodiment in any way.

Influenza Virus

Influenza viruses have a segmented single-stranded (negative or antisense) genome. The influenza virion consists of an internal ribonucleoprotein core containing the single-stranded RNA genome and an outer lipoprotein envelope lined by a matrix protein. The segmented genome of influenza A consists of eight linear RNA molecules that encode ten polypeptides. Two of the polypeptides, HA and NA include the primary antigenic determinants or epitopes required for a protective immune response against influenza. Based on the antigenic characteristics of the HA and NA proteins, influenza strains are classified into subtypes. For example, recent outbreaks of avian influenza in Asia have been categorized as H5N1, H7N7 and H9N2 based on their HA and NA phenotypes. These subtypes have proven highly infectious in poultry and have been able to jump the species barrier to directly infect humans causing significant morbidity and mortality.

HA is a surface glycoprotein which projects from the lipoprotein envelope and mediates attachment to and entry into cells. The HA protein is approximately 566 amino acids in length, and is encoded by an approximately 1780 base polynucleotide sequence of segment 4 of the genome. Polynucleotide and amino acid sequences of HA (and other influenza antigens) isolated from recent, as well as historic, avian influenza strains can be found, e.g., in the GENBANK® database (available on the world wide web at ncbi.nlm.nih.gov/entrez). For example recent avian H5 subtype HA sequences include: AY075033, AY075030, AY818135, AF046097, AF046096, and AF046088; recent H7 subtype HA sequences include: AJ704813, AJ704812, and 247199; and, recent avian H9 subtype HA sequences include: AY862606, AY743216, and AY664675. One of ordinary skill in the art will appreciate that essentially any previously described or newly discovered avian HA antigen can be utilized in the compositions and methods described herein. Typically, the appropriate HA sequence or sequences are selected based on circulating or predicted avian and/or pandemic HA subtypes, e.g., as recommended by the World Health Organization.

In addition to the HA antigen, which is the predominant target of neutralizing antibodies against influenza, the neuraminidase (NA) envelope glycoprotein is also a target of the protective immune response against influenza. NA is an approximately 450 amino acid protein encoded by an approximately 1410 nucleotide sequence of influenza genome segment 6. Recent pathogenic avian strains of influenza have belonged to the N1, N7 and N2 subtypes. Exemplary NA polynucleotide and amino acid sequences include, e.g., N1: AY651442, AY651447, and AY651483; N7: AY340077, AY340078 and AY340079; and, N2: AY664713, AF508892 and AF508588. Additional NA antigens can be selected from among previously described or newly discovered NA antigens based on circulating and/or predicted avian and/or pandemic NA subtypes.

The remaining segments of the influenza genome encode the internal proteins. While immunization with internal proteins alone does not give rise to a substantially protective neutralizing antibody response, T-cell responses to one or more of the internal proteins can significantly contribute to protection against influenza infection. Compared to the polymorphic HA and NA antigens, the internal proteins are more highly conserved between strains, and between subtypes. Thus, a T cell receptor elicited by exposure to an internal protein of an avian or human subtype of influenza binds to the comparable internal protein of other avian and human subtypes.

PB2 is a 759 amino acid polypeptide which is one of the three proteins which comprise the RNA-dependent RNA polymerase complex. PB2 is encoded by approximately 2340 nucleotides of the influenza genome segment 1. The remaining two polymerase proteins, PB1, a 757 amino acid polypeptide, and PA, a 716 amino acid polypeptide, are encoded by a 2341 nucleotide sequence and a 2233 nucleotide sequence (segments 2 and 3), respectively.

Segment 5 consists of 1565 nucleotides encoding a 498 amino acid nucleoprotein (NP) protein that forms the nucleocapsid. Segment 7 consists of a 1027 nucleotide sequence encoding a 252 amino acid M1 protein, and a 96 amino acid M2 protein, which is translated from a spliced variant of the M RNA. Segment 8 consists of a 890 nucleotide sequence encoding two nonstructural proteins, NS 1 and NS2.

Of these proteins, the M (M1 and M2) and NP proteins are most likely to elicit protective humoral and/or cellular T cell responses. Accordingly, while any of the internal proteins can be included (for example, in addition to one or more avian HA and/or NA antigens) in the compositions and methods described herein, adenovirus vectors and adenoviruses commonly also include one or more of M1, M2 and/or NP proteins. As responses against internal protein(s) of one strain of virus tend to interact with internal protein(s) of other strains of influenza, the internal protein can be selected from essentially any avian and/or human strain. For example, the internal protein(s) can be selected from avian H5N1, H7N7 and/or H9N2 strains. Alternatively, the internal protein(s) can be selected from human H3N2, H1N1, and/or H2N2. Exemplary internal protein polynucleotide and amino acid sequences can be found, e.g., in GENBANK®. For example, H3N2 M and NP nucleic acids and proteins are represented by Accession Nos. AF255370 and CY000756, respectively. The internal proteins of influenza are more conserved between strains and tend to elicit a cross-reactive T cell response that contributes to the protective immune response against influenza.

It will be appreciated by those of skill in the art that the specific nucleic acids and proteins indicated above by accession number are non-exclusive examples, and numerous additional influenza antigen sequences can be expressed in the context of the adenovirus vectors disclosed herein. For example, additional influenza antigens, and the nucleic acids encoding them are commonly similar in primary structure to the antigens and nucleic acids referenced above. The similarity between amino acid (and polynucleotide) sequences is expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid sequences, the more similar are the higher order structures resulting from folding and assembly. Thus, for example, HA antigens of the same influenza subtype typically share a high degree of sequence identity. Variants of an HA antigen (of a particular subtype) can have one or a small number of amino acid deletions, additions or substitutions but will nonetheless share a very high percentage of their amino acid (and generally their polynucleotide sequence). To the extent that variants of a subtype differ from each other, their overall antigenic characteristics are maintained. In contrast, HA antigens of different subtypes share less sequence identity (e.g., at the receptor binding pocket) and/or differ from each other such that their antigenic characteristics are no longer identical.

Methods of determining sequence identity are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993 and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

Thus, the adenovirus vectors disclosed herein can include and/or express any of numerous influenza antigens, such as variants of H5, H7 and/or H9 subtype hemagglutinin antigens (or other antigens discussed herein) that are similar in sequence, as measured by sequence similarity or hybridization measures indicated above.

Adenovirus Vectors

The term "adenovirus" as used herein is intended to encompass all adenoviruses, including the Mastadenovirus and Aviadenovirus genera. To date, at least forty-seven human serotypes of adenoviruses have been identified (see, e.g., FIELDS et al., VIROLOGY, volume 2, chapter 67 (3d ed., Lippincont-Raven Publishers). Adenoviruses are linear double-stranded DNA viruses approximately 36 kb in size. Their genome includes an inverted sequence (ITR) at each end, an encapsidation sequence, early genes and late genes. The main early genes are contained in the E1, E2, E3 and E4 regions. Among them, the genes contained in the E1 region (E1a and E1b, in particular) are necessary for viral replication. The E4 and L5 regions, for example, are involved in viral propagation, and the main late genes are contained in the L1 to L5 regions. For example, the human Ad5 adenovirus genome has been sequenced completely and the sequence is available on the world wide web, (see, for example, GENBANK® Accession No. M73260). Similarly, portions, or in some cases the whole, of the genome of human and non-human adenoviruses of different serotypes (Ad2, Ad3, Ad7, Ad12, and the like) have also been sequenced.

Upon infection of a subject (or host) with recombinant adenoviruses, or introduction of a recombinant adenovirus vector, exogenous nucleic acids contained within the adenovirus genome are transcribed, and translated, by the host cell RNA polymerase and translational machinery. Thus, a polynucleotide sequence that encodes one or more influenza antigens can be incorporated into an adenovirus vector and introduced into the cells of a subject where the polynucleotide sequence is transcribed and translated to produce the influenza antigen. Recently, non-replicating adenovirus vectors have been used to produce and deliver an immunologically effective HA1 strain vaccine (Van Kampen et al., *Vaccine* 23:1029-1036, 2005). In the context of the compositions and methods described herein, a polynucleotide sequence that encodes at least one avian influenza antigen (as described above, such as a hemagglutinin antigen of H5, H7 or H9 subtype) is incorporated into an adenovirus vector using established molecular biology procedures. Nucleic acids (e.g., cDNAs) that encode influenza antigens can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Exemplary procedures sufficient to guide one of ordinary skill in the art through the production of a recombinant adenovirus vector that includes a polynucleotide sequence that encodes one (or more than one) influenza antigen can be found in Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology,* 4th ed., Wiley & Sons, 1999.

Typically, the polynucleotide sequence encoding the influenza antigen(s) is operably linked to transcriptional control sequences including, e.g., a promoter and a polyadenylation signal. A promoter is a polynucleotide sequence recognized by the transcriptional machinery of the host cell (or introduced synthetic machinery), that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters known in the art include viral promoters, including those of the cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, dendritic cell-specific promoters, such as CD11c, macrophage-specific promoters, such as CD68, Langerhans cell-specific promoters, such as Langerin, and promoters specific for keratinocytes, and epithelial cells of the skin and lung.

The promoter can be either inducible or constitutive. An inducible promoter is a promoter which is inactive or exhibits low activity except in the presence of an inducer substance. Some examples of promoters that may be included as a part of the present invention include, but are not limited to, MT II, MMTV, collagenase, stromelysin, SV40, murine MX gene, .alpha.-2-macroglobulin, MHC class I gene h-2kb, HSP70, proliferin, tumor necrosis factor, or thyroid stimulating hormone gene promoter. Typically, however, the promoter is a constitutive promoter that results in high levels transcription upon introduction into a host cell in the absence of additional factors. Optionally, the transcription control sequences include one or more enhancer elements, which are binding recognition sites binds for one or more transcription factors that increase transcription above that observed for the minimal promoter alone.

Often it is also desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

Typically, a polynucleotide sequence that encodes an influenza antigen will be a full length open reading frame including a translation initiation site. However, it is also possible to use polynucleotide sequences that encode an immunogenic portion (subportion) of the antigen. If the polynucleotide sequence lacks a translation initiation site or codon, one can be introduced at an appropriate site preceding the polynucleotide sequence encoding an antigen subportion during production of the vector.

Nucleic acid vectors encoding adenoviruses are well-known in the art, and have been utilized for gene therapy and vaccine applications. Exemplary adenovirus vectors are described in Berkner, *BioTechniues* 6:616-629, 1988; Graham, *Trend Biotechnol,* 8:85-87, 1990; Graham & Prevec, in *Vaccines: new approaches to immunological problems*, Ellis (ed.), pp. 363-90, Butterworth-Heinemann, Woburn, 1992; Mittal et al., in *Recombinant and Synthetic Vaccines*, Talwar et al., (eds) pp. 362-366, Springer Verlag, New York, 1994; Rasmussen et al., *Hum. Gene Ther.* 16:2587-2599, 1999; Hitt & Graham, *Adv. Virus Res.* 55:479-505, 2000, Published US Patent Application 2002/0192185, which are incorporated herein in their entirety.

Generally, the vectors are modified to make them replication defective, that is, incapable of replicating autonomously in the host cell, although in addition to such helper dependent adenovirus vectors, conditional replication competent and replication competent adenovirus vectors and viruses can also be used. Generally, the genome of replication defective viruses lack at least some of the sequences necessary for replication of the virus in an infected cell. These regions may be either removed (wholly or partially), or rendered non-functional, or replaced by other sequences, and in particular by a sequence coding for a molecule of therapeutic interest. Typically, the defective virus retains the sequences which are involved in encapsidation of viral particles.

Replication defective adenoviruses typically include a mutation, such as a deletion, in one or more of the E1 (E1a and/or E1b), E3 region, E2 region and/or E4 region—have been deleted. The entire adenovirus genome except the ITR and packaging elements can be deleted and the resultant adenovirus vectors and know as helper-dependent vectors or "gutless" vectors. In some cases a heterologous DNA sequences are inserted in place of the deleted adenovirus sequence (Levrero et al., *Gene* 101:195-202, 1991; Ghosh-Choudhury et al., *Gene* 50:161-171, 1986). Other constructions contain a deletion in the E1 region and of a non-essential portion of the E4 region (WO 94/12649). Exemplary adenovirus vectors are also described in U.S. Pat. Nos. 6,328,958, 6,669,942 and 6,420,170, which are incorporated herein by reference.

These replication defective recombinant adenoviruses may be prepared in different ways, for example, in a competent cell line capable of complementing all the defective functions essential for replication of the recombinant adenovirus. For example, adenoviruses vectors can be produced in a complementation cell line (such as 293 cells) in which a portion of the adenovirus genome has been integrated. Such cells lines contains the left-hand end (approximately 11-12%) of the adenovirus serotype 5 (Ad5) genome, comprising the left-hand ITR, the encapsidation region and the E1 region, including E1a, E1b and a portion of the region coding for the pIX protein. This line is capable of trans-complementing recombinant adenoviruses which are defective for the E1 region. Typically, expression of both E1A and E1B proteins is needed for E1 complementation.

Human adenovirus vectors are commonly utilized to introduce exogenous nucleic acids into human and animal cells and organisms. Adenoviruses exhibit broad host cell range, and adenovirus vectors can be utilized to infect human as well as non-human animal, including birds. Most commonly, the human adenovirus vectors are HAd5 vectors derived from adenovirus serotype 5 viruses. Due to the large size of the intact adenovirus genome, insertion of heterologous polynucleotide sequences is most conveniently performed using a shuttle plasmid. Sequences, such as those influenza antigens are cloned into a shuttle vector which then undergoes homologous recombination with all or part of an adenovirus genome in cultured cells. In addition, homologous recombination can also be done in bacteria to generate full length adenovirus vectors.

In some cases, it is desirable to use non-human adenovirus vectors to avoid pre-existing host immunity to human adenoviruses. Infection with human adenovirus is common in human populations, and many or most individuals have circulating antibody titers that will bind and neutralize a recombinant human adenovirus. Thus, in at least some proportion of the human population vaccination with human adenovirus vectors will not result in efficient generation of an immune response against influenza due to neutralization of the vector containing the influenza sequences. To avoid this problem, non-human adenovirus vectors can be used to circumvent any pre-existing immunity against human adenovirus.

Adenoviruses of animal origin are also capable of infecting human, as well as non-human, cells efficiently, and following infection are generally incapable of propagating in human cells (see, Application WO 94/26914). Thus, adenoviruses of animal origin can be used in the context of the vectors and viruses described herein. The use of animal adenovirus vectors for human and animal vaccine development is discussed in detail in Bangari & Mittal, *Vaccine* 24:849-862, 2006, which is incorporated herein by reference. For example animal adenovirus vectors can be selected from canine, bovine, murine (for example: MAV1, Beard et al., *Virology* 75:81, 1990), ovine, porcine, avian (e.g., chicken) or alternatively simian (for example: SAV) adenoviruses. For example, bovine and porcine adenoviruses can be used to produce adenovirus vectors that express influenza antigens, including various bovine serotypes available from the ATCC (types 1 to 8) under the references ATCC VR-313, 314, 639-642, 768 and 769, and porcine adenovirus 5359. Additionally, simian adenoviruses of various serotypes, including SAd25, SAd22, SAd23 and SAd24, such as those referenced in the ATCC under the numbers VR-591-594, 941-943, 195-203, and the like, several serotypes (1 to 10) of avian adenovirus which are available in the ATCC, such as, the strains Phelps (ATCC VR-432), Fontes (ATCC VR-280), P7-A (ATCC VR-827), IBH-2A (ATCC VR-828), J2-A (ATCC VR-829), T8-A (ATCC VR-830), K-11 (ATCC VR-921) and strains referenced as ATCC VR-831 to 835, as well as murine adenoviruses FL (ATCC VR-550) and E20308 (ATCC VR-528), and ovine adenovirus type 5 (ATCC VR-1343) or type 6 (ATCC VR-1340) can be used.

For example, both bovine and porcine adenovirus vectors are capable of infecting human cells, and can be used as vectors to express avian influenza antigens. Exemplary bovine and porcine adenovir lished US patent application no. 2002/0192185, and in U.S. Pat. Nos. 6,492,343 and 6,451,319, which are incorporated herein by reference.

The compositions and methods described herein are applicable to any influenza antigens. In particular, the compositions and methods can be employed to express, and to generate an immune response against avian strains of influenza. For example, the adenovirus vectors, recombinant adenoviruses and immunogenic compositions disclosed herein can include an HA antigen of any avian or pandemic strain of influenza. Numerous avian HA antigens have been identified, and the sequences can be obtained, for example using the publicly available NCBI database (on the world wide web at ncbi.nlm.nih.gov/entrez/query.fcgi). Exemplary HA antigens from recent avian flu outbreaks are represented by AY818135 (A/Viet Nam/1203/04); AF084280 (A/Hong Kong/483/97); AF036356 (A/Hong Kong/156/97); AY575870 (A/Hong Kong/213/03). Nucleic acids including these sequences can be obtained by cloning and/or amplification from virus isolates, or can be produced synthetically. Similarly, novel HA antigens isolated from newly emergent strains or newly isolated strains can also be included in the compositions described herein. Likewise, NA antigens of avian known or newly discovered avian strains can be incorporated into the vectors, viruses and compositions described herein. Optionally, the viruses, vectors and/or immunogenic compositions include one or more internal proteins of an avian or non-avian, e.g., human influenza strain.

Recombinant adenovirus expressing avian and/or other influenza antigens can be produced from the vectors described above following introduction of the adenovirus vector into a suitable host cell. In the case of replication defective vectors, the adenovirus vector is typically introduced into a cell line that complements the defective function. For example, E1 deficient virus can be grown in a cell line that complements E1 function due to expression of an introduced nucleic acid that encodes adenovirus E1 protein. Exemplary cell lines include both human and non-human cell lines that have been engineered to express an adenovirus E1 (e.g., E1A) proteins. For example, 293 cells that express adenovirus E1 proteins are commonly utilized to grow recombinant replication-defective adenoviruses that have a deletion of the E1 region. Additional suitable cell lines include MDBK-221, FBK-34, and fetal retinal cells of various origins. Specific examples of cell lines suitable for growing porcine and bovine recombinant adenovirus include FPRT-HE1-5 cells (Bangari & Mittal, *Virus Res.* 105:127-136, 2004) and FBRT-HE1 cells (van Olphen et al., *Virology,* 295:108-118, 2002), respectively. In certain embodiments, the cell express adenovirus E1 genes of more than one strain of virus, such as 2 or more different strains of virus with different species tropism. For example, the cells can express E1 genes of a human and a non-human (e.g., pig and/or cow E1 genes). Those of ordinary skill in the art will readily be able to select or produce suitable additional or alternative cell lines that complement the replication functions of replication-defective adenovirus vectors. For example, any of the various mammalian cell lines disclosed herein (or known in the art) can be transfected with E1 and/or E3 genes of any of the strains of adenovirus, such as the exemplary strains disclosed herein, based on the particular adenovirus vector to be grown. For example, it is common to select E1 (and/or E3) genes that correspond to (that is, are from the same or a functionally similar strain) the same strain as the adenovirus vector. One of skill in the art will also appreciate that functionally similar variants (such as variants that share substantial sequence identity, or that specifically hybridize, e.g., under high stringency conditions) to any of the exemplary adenovirus genes, can also be used to produce cell lines that support the growth of adenovirus vectors that encode influenza antigens.

One common method for producing replication defective adenovirus vectors that incorporate exogenous nucleic acids is described in Ng et al., *Hum. Gene Ther.* 10:2667-2672, 1999, and *Hum. Gene Ther.* 11:693-699, 2000, which are incorporated herein in their entirety. Briefly, to produce a human adenovirus vector containing an influenza antigen, a polynucleotide sequence encoding an influenza antigen (for example, one or more avian HA antigens) operably linked to a strong promoter (such as the CMV immediate early promoter) is inserted into a shuttle vector, such as pDC311. The pDC311 shuttle vector is a plasmid that contains the left end of HAd5 (approximately 4 kb) with a 3.1 kb E1 deletion, a loxP site for site specific recombination in the presence of Cre recombinase and an intact packaging signal ($\psi$). The shuttle vector is co-transfected into appropriate cells that express the Cre recombinase (e.g., 293 Cre cells) along with a plasmid that includes a replication defective HAd5 genome (e.g., containing deletions in the E1 and/or E3 region genes) that lacks a packaging signal, and contains a loxP site. Homologous Cre mediated recombination results in the production of an adenovirus vector plasmid that encodes a replication defective adenovirus that expresses the inserted influenza antigen.

Cells that express complementing replication function (such as E1 when the replication defective adenovirus vector lacks E1 function) can be transfected with a recombinant adenovirus vector according to standard procedures, such as electroporation, calcium phosphate precipitation, lipofection, etc., or infected with adenovirus at low infectivity (e.g., between 1-1000 p.f.u./cell). In some cases confluent monolayers of cells are utilized, e.g., in 60 mm dishes. The cells are then incubated (grown) for a period of time sufficient for expression and replication of adenovirus, and the cells are divided to maintain active growth and maximize virus recovery, prior to harvesting of recombinant adenovirus. Typically following several passages (for example, 2-5 passages), recombinant is collected by lysing the cells to release the virus, and then concentrating the virus. Recombinant adenovirus can be concentrated by passing the lysate containing the virus over a density gradient (such as a CsCl density gradient). Following concentration the recombinant adenoviruses are typically dialyzed against a buffer (such as 10 mM Tris pH 8.0, 2 mM $MgCl_2$, 5% sucrose), titered and stored until use at −80° C. Methods for producing adenovirus at a large scale, e.g., suitable for preparation of immunogenic compositions to be used as vaccines are described, e.g., in published US patent application no. 20030008375, which is incorporated herein by reference.

Production of Recombinant Influenza Virus Antigens from Adenovirus Vectors.

In addition to their utility in the production of immunogenic compositions containing adenovirus vector nucleic acids and/or adenovirus that are capable of expressing avian influenza antigens, the adenovirus vectors disclosed herein can be used for the production and manufacture of recombinant influenza antigens, such as recombinant HA antigens from highly pathogenic avian strains of influenza as well as other influenza antigens. Methods for producing recombinant antigens using human and non-human adenovirus vectors are well known in the art, and exemplary compositions and methods are described in, for example, U.S. Pat. Nos. 5,824,770, 6,319,716, and 6,824,770, which are incorporated herein in their entirety. Additionally, commercially available vectors, such as the ADEASY™ adenovirus vector system from Stratagene (La Jolla, Calif.) can be employed to produce adenovirus vectors and adenovirus recombinants (recombinant adenovirus) that are capable of expressing recombinant influenza proteins.

As discussed above, the adenovirus vectors contain a heterologous polynucleotide sequence that encodes one or more avian influenza virus antigen(s) in place of the E1 and/or E3 gene region of the adenovirus vector. Optionally, two, or even three or more influenza antigens are encoded by the heterologous nucleic acid. Conversely, fragments of influenza antigens containing immunogenic epitopes can be encoded by the polynucleotide sequence inserted into the adenovirus vector. Typically, the polynucleotide sequence encoding the influenza antigen(s) is operably linked to transcription regulatory sequences (e.g., a promoter and/or enhancer elements, and/or polyadenylation sequences) capable of producing high levels of expression. A number of eukaryotic promoter and polyadenylation sequences which provide successful expression of foreign genes in mammalian cells and how to construct expression cassettes, are known in the art, for example in U.S. Pat. No. 5,151,267, the disclosures of which are incorporated herein by reference. The promoter is selected to give optimal expression of immunogenic protein which in turn satisfactorily leads to humoral, cell mediated and mucosal immune responses according to known criteria.

Optionally, the polynucleotide encoding an influenza antigen includes a portion that encodes a peptide (e.g., an epitope) or polypeptide tag to facilitate subsequent purification of the recombinant antigen. Typically, the influenza antigen is expressed as a fusion protein in which the influenza antigen is linked to one or more peptide (or polypeptide) domains that facilitate expression and/or purification. Numerous suitable tags are known in the art, and expressed proteins that include such tags can readily be isolated using commercially available reagents and kits. If desired, the tag can be removed from the antigen, for example by enzymatic or chemical cleavage, before the recombinant antigen is used in subsequent applications. Exemplary tags include Myc epitope tags, Histidine tags and GST tags.

The recombinant adenovirus vector containing one or more influenza virus antigen(s) can be expressed in cell lines into which has been introduced an expression cassette encoding a complementary E1 region (and/or an E2 region). These recombinant cell lines are capable of allowing a recombinant adenovirus, having an E1 gene region deletion replaced by heterologous nucleotide sequence encoding one or more influenza antigen(s) or fragments thereof, to replicate and express the desired foreign-gene or fragment, which is encoded by the recombinant adenovirus. Optionally, such a cell line can include E1 (and/or E2) genes corresponding to more than one strain of adenovirus. For example, suitable cell lines include those that contain nucleic acids that express E1 of a human adenovirus as well as, for example, E1 of a porcine or bovine adenovirus strain.

For use in pharmaceutical compositions, recombinant influenza antigens are typically purified following expression in cultured cells. Methods for isolated recombinant proteins expressed in cultured cells are well known in the art, and specific methods are described in Sambrook et al. (In *Molecular Cloning: A Laboratory Manual*, CSHL, New York, 2001) and in Brent et al., *Current Protocols in Molecular Biology*, John Wiley and Sons, New York, 2003). One skilled in the art will understand that there are myriad ways to purify recombinant polypeptides, and such typical methods of protein purification may be used to purify influenza antigens expressed from adenovirus vectors. Such methods include, for instance, protein chromatographic methods including ion exchange, gel filtration, HPLC, monoclonal antibody affinity chromatography and isolation of insoluble protein inclusion bodies after over production. In addition, purification can be based on attached tags (as discussed above), for instance a six-histidine sequence, may be recombinantly fused to the protein and used to facilitate polypeptide purification using Nickel affinity columns (such as, nickel-nitrilotriacetic acid (Ni-NTA) metal affinity chromatography matrix (*The QIAexpressionist*, QIAGEN, 1997).

If desired, the recombinant influenza antigen(s) can be conjugated to a vaccine carrier for administration to a subject. Vaccine carriers are well-known in the art: for example, bovine serum albumin (BSA), human serum albumin (HSA) keyhole limpet hemocyanin (KLH), and rotavirus VP6. In some cases one or more adjuvant, such as alum, is combined with the recombinant influenza antigen(s) for administration to a subject, as discussed below.

Immunogenic Compositions Comprising Adenovirus Vectors and Recombinant Adenovirus.

The recombinant adenovirus vectors and recombinant adenoviruses that express influenza antigens (e.g., avian influenza antigens) can be administered in vitro, ex vivo or in vivo to a cell or subject. Generally, it is desirable to prepare the vectors or viruses as pharmaceutical compositions appropriate for the intended application. Accordingly, methods for making a medicament or pharmaceutical composition containing the adenovirus vectors or adenoviruses described above are included herein. Typically, preparation of an pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

Pharmaceutical (for example, immunogenic) compositions typically include an effective amount of the adenovirus vector or virus dispersed (for example, dissolved or suspended) in a pharmaceutically acceptable carrier or excipient. The phrases "pharmaceutically acceptable" or "pharmacologically acceptable" refer to molecular entities and compositions that do not produce an adverse, allergic or other undesirable reaction when administered to a human or animal subject. Numerous pharmaceutically acceptable carriers and/or pharmaceutically acceptable excipients are known in the art and are described, e.g., in *Remington's Pharmaceutical Sciences*, by E. W. Martin, Mack Publishing Co., Easton, Pa., 15th Edition (1975).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the immunogenic compositions is contemplated. Supplementary active ingredients also can be incorporated into the compositions. For example, certain pharmaceutical compositions can include the vectors or viruses in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical compositions (medicaments) can be prepared for use in prophylactic regimens (e.g., vaccines) and administered to human or non-human subjects (including birds, such as domestic fowl, e.g., chickens, ducks, guinea fowl, turkeys and geese) to elicit an immune response against an influenza antigen (or a plurality of influenza antigens). Thus, the pharmaceutical compositions typically contain an immunologically effective amount of the adenovirus vector or adenovirus (or indeed of recombinant influenza antigen produced by expressing an adenovirus vector as disclosed herein). An immunologically effective amount, e.g., of a vaccine composition, is an amount sufficient to elicit a desired immune response, such as a protective immune response in an immunocompetent subject, when administered in one or more doses. Typically, an immunologically effective amount of a vaccine is administered to a subject in one or more doses, prior to exposure (that is, prophylactically) to an infectious agent (such as an influenza virus) to elicit a protective immune response against the infectious agent. In this context, adenovirus vectors and/or adenoviruses containing avian influenza antigens (and/or recombinant influenza antigens produced by expressing such adenoviruses) can be administered to a subject in one or more doses to elicit a protective response against avian and/or pandemic influenza.

In some cases the compositions are administered following infection to enhance the immune response, in such applications, the pharmaceutical composition is administered in a therapeutically effective amount. A therapeutically effective amount is a quantity of a composition used to achieve a desired effect in a subject. For instance, this can be the amount of the composition necessary to inhibit viral replication or to prevent or measurably alter outward symptoms of viral infection. When administered to a subject, a dosage will generally be used that will achieve target tissue concentrations (for example, in lymphocytes) that has been shown to achieve an in vitro or in vivo effect.

For example, the compositions described herein can be administered to a human (or non-human) subject to elicit an immune response against avian influenza virus, e.g., a pathogenic H5N1, H7N7 or H9N2 strain of avian influenza virus. Generally, the adenovirus vectors and/or adenoviruses described herein elicit a protective or partially protective immune response against at least one strain or subtype of avian (or pandemic) influenza. That is, the pharmaceutical compositions described herein are typically capable of preventing influenza, or of decreasing the severity of symptoms (e.g., morbidity and/or mortality) following subsequent exposure to a pathogenic strain of virus in at least a significant portion of the population to which the composition is administered. In some cases, the immune response is protective or partially protective against multiple strains, or even multiple subtypes of avian (or pandemic) influenza, including their administration to humans and non-human subjects (including birds).

Typically, a protective immune response against influenza involves the production of neutralizing antibodies that bind to the HA antigen. Because these antigens are highly polymorphic and antibodies raised against one subtype are typically not protective against influenza of another subtype, the immunogenic pharmaceutical compositions described herein can include adenovirus vectors or adenoviruses that express more than one HA antigen, e.g., by one or more vectors or viruses. As previously discussed, the HA antigens can be variants of a single subtype or of more than one HA subtype. Optionally, an adenovirus that expresses (or a vector that encodes) an NA antigen is also administered.

T-cell responses against influenza antigens broaden the immune response against influenza, increasing vaccine efficacy. Internal proteins, such as the M2 and NP proteins of influenza A possess suitable B-cell and/or T-cell epitopes, and when administered in combination with antigenic polypeptides, such as HA and NA antigens, elicit a T cell response that increases protection and contributes to reduced morbidity due to influenza infection. Furthermore, such internal protein epitopes are more highly conserved between influenza subtypes offering cross protection against multiple strains of avian and human influenza. Accordingly, pharmaceutical compositions that include one or more adenovirus vectors or adenoviruses that express influenza internal protein(s) can be administered to elicit an influenza specific immune response.

Administration of therapeutic compositions including recombinant adenovirus that expresses an influenza antigen (including an avian influenza antigen) can be by any common route as long as the target tissue (typically, the respiratory tract) is available via that route. This includes oral, nasal, ocular, buccal, or other mucosal (e.g., rectal, vaginal) or topical administration. Alternatively, administration will be by orthotopic, intradermal subcutaneous, intramuscular, intraperitoneal, or intravenous injection routes. Such immunogenic compositions are usually administered as pharmaceutically acceptable compositions that include physiologically acceptable carriers, buffers or other excipients.

The immunogenic compositions can also be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations which are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders. Exemplary formulations can be found in US patent publication no. 20020031527, the disclosure of which is incorporated herein by reference. When the route is topical, the form may be a cream, ointment, salve or spray. Exemplary methods for intramuscular, intranasal and topical administration of the adenovirus vectors and adenoviruses described herein can be found, e.g., in U.S. Pat. No. 6,716,823, which is incorporated herein by reference.

Optionally, the pharmaceutical compositions or medicaments can include a suitable adjuvant to increase the immune response against the influenza antigen(s). As used herein, an "adjuvant" is any potentiator or enhancer of an immune response. The term "suitable" is meant to include any substance which can be used in combination with the adenovirus vector or adenovirus to augment the immune response, without producing adverse reactions in the vaccinated subject. Effective amounts of a specific adjuvant may be readily determined so as to optimize the potentiation effect of the adjuvant on the immune response of a vaccinated subject. For example, 0.5%-5% (e.g., 2%) aluminum hydroxide (or aluminum phosphate) and MF-59 oil emulsion (0.5% polysorbate 80 and 0.5% sorbitan trioleate. Squalene (5.0%) aqueous emulsion) are adjuvants which have been favorably utilized in the context of influenza vaccines. Other adjuvants include mineral, vegetable or fish oil with water emulsions, incomplete Freund's adjuvant, E. coli J5, dextran sulfate, iron oxide, sodium alginate, Bacto-Adjuvant, certain synthetic polymers such as Carbopol (BF Goodrich Company, Cleveland, Ohio), poly-amino acids and co-polymers of amino acids, saponin, carrageenan, REGRESSIN (Vetrepharm, Athens, Ga.), AVRIDINE (N,N-dioctadecyl-N',N'-bis(2-hydroxyethyl)-propanediamine), long chain polydispersed.beta. (1,4) linked mannan polymers interspersed with O-acetylated groups (e.g. ACEMANNAN), deproteinized highly purified cell wall extracts derived from non-pathogenic strain of *Mycobacterium* species (e.g. EQUIMUNE, Vetrepharm Research Inc., Athens Ga.), Mannite monooleate, paraffin oil and muramyl dipeptide. A suitable adjuvant can be selected by one of ordinary skill in the art.

An effective amount of the immunogenic composition is determined based on the intended goal, for example vaccination of a human or non-human subject. The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes nucleic acids or viruses. Generally, the immunogenic compositions described herein are administered for the purpose of eliciting an immune response against an influenza antigen (or antigens) or an influenza virus. Accordingly, the dose is typically an immunologically effective amount of the recombinant adenovirus.

A typical dose of a recombinant adenovirus that expresses an influenza antigen is from 10 p.f.u. to $10^{15}$ p.f.u./administration. For example, a pharmaceutical composition can include from about 100 p.f.u. of a recombinant adenovirus, such as about 1000 p.f.u., about 10,000 p.f.u., or about 100,000 p.f.u. of each recombinant adenovirus in a single dosage. Optionally, a pharmaceutical composition can include at least about a million p.f.u. or more per administration. For example, in some cases it is desirable to administer about $10^7$, $10^8$, $10^9$ or $10^{10}$ p.f.u. of recombinant adenovirus that expresses a particular influenza antigen. In some cases, for example, where a single adenovirus is administered, a higher dosage of virus is administered to a subject, for example, when a recombinant virus that expresses multiple influenza antigens is administered. Alternatively, when several adenovirus, each of which expresses a different influenza antigen(s), is administered, fewer of each virus is administered, although the total dose of virus may nonetheless be upwards of $10^8$, or greater than $10^9$, or $10^{10}$ p.f.u.

In addition, adenovirus vectors (nucleic acid vectors) can be administered. For example, when administering a nucleic acid vaccine including an adenovirus vector that encodes an influenza antigen, facilitators of nucleic acid uptake and/or expression can also be included, such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, e.g., *Liposomes: A Practical Approach*, RPC New Ed., IRL Press, 1990). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the tradename LIPOFECTIN®., and DOTAP (1,2-bis(oleyloxy)-3-(trimethylammonio)propane), see, e.g., Felgner et al., *Proc. Natl. Acad. Sci. USA* 84:7413-7416, 1987; Malone et al., *Proc. Natl. Acad. Sci. USA* 86:6077-6081, 1989; U.S. Pat. Nos. 5,283,185 and 5,527,928, and International Publication Nos WO 90/11092, WO 91/15501 and WO 95/26356. These cationic lipids may preferably be used in association with a neutral lipid, for example DOPE (dioleyl phosphatidylethanolamine)-. Still further transfection-facilitating compositions that can be added to the above lipid or liposome preparations include spermine derivatives (see, e.g., International Publication No. WO 93/18759) and membrane-permeabilizing compounds such as GALA, Gramicidine S and cationic bile salts (see, e.g., International Publication No. WO 93/19768).

Alternatively, nucleic acids (adenovirus vectors) encoding avian influenza viral genes can be encapsulated, adsorbed to, or associated with, particulate carriers. Suitable particulate carriers include those derived from polymethyl methacrylate polymers, as well as PLG microparticles derived from poly (lactides) and poly(lactide-co-glycolides). See, e.g., Jeffery et al., *Pharm. Res.* 10:362-368, 1993. Other particulate systems and polymers can also be used, for example, polymers such as polylysine, polyarginine, polyornithine, spermine, spermidine, as well as conjugates of these molecules.

The formulated vaccine compositions will thus typically include a polynucleotide (e.g. a plasmid) containing an adenovirus that includes a polynucleotide sequence encoding an avian influenza antigen in an amount sufficient to mount an immunological response. An appropriate effective amount can be readily determined by one of skill in the art. Such an amount will fall in a relatively broad range that can be determined through routine trials. For example, immune responses have been obtained using as little as 1 μg of DNA, while in other administrations, up to 2 mg of DNA has been used. It is generally expected that an effective dose of polynucleotides containing the genomic fragments will fall within a range of about 10 μg to 1 mg, however, doses above and below this range may also be found effective.

Adenovirus vector nucleic acids can be coated onto carrier particles (e.g., core carriers) using a variety of techniques known in the art. Carrier particles are selected from materials which have a suitable density in the range of particle sizes typically used for intracellular delivery from an appropriate particle-mediated delivery device. The optimum carrier particle size will, of course, depend on the diameter of the target cells. Alternatively, colloidal gold particles can be used wherein the coated colloidal gold is administered (e.g., injected) into tissue (e.g., skin or muscle) and subsequently taken-up by immune-competent cells.

Tungsten, gold, platinum and iridium carrier particles can be used. Tungsten and gold particles are preferred. Tungsten particles are readily available in average sizes of 0.5 to 2.0 μm in diameter. Although such particles have optimal density for use in particle acceleration delivery methods, and allow highly efficient coating with DNA, tungsten may potentially be toxic to certain cell types. Gold particles or microcrystalline gold (e.g., gold powder A1570, available from Engelhard Corp., East Newark, N.J.) will also find use with the present methods. Gold particles provide uniformity in size (available from Alpha Chemicals in particle sizes of 1-3 μm, or available from Degussa, South Plainfield, N.J. in a range of particle sizes including 0.95 μm) and reduced toxicity.

A number of methods are known and have been described for coating or precipitating DNA or RNA onto gold or tungsten particles. Most such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in a suitable particle delivery instrument, such as a gene gun. Alternatively, nucleic acid vaccines can be administered via a mucosal membrane or through the skin, for example, using a transdermal patch. Such patches can include wetting agents, chemical agents and other components that breach the integrity of the skin allowing passage of the nucleic acid into cells of the subject.

In addition to adjuvants, which typically potentiate or enhance an immune response in a non-specific manner, for example by concentrating or slowing diffusion of an antigen, genetic immunstimulatory agents can be included in the pharmaceutical compositions along with adenovirus vectors or adenoviruses to enhance the anti-avian influenza immune response. For example, certain CpG oligonucleotides (such as 5'-tccatgagcttcctgatcct-3' (SEQ ID NO:1); 5'-tccatgacgttc-ctgacgtt-3' (SEQ ID NO:2) and 5'-tgactgtgaacgttcgagatga-3' (SEQ ID NO:3) have been shown to be potent immunostimulatory molecules when administered in conjunction with an antigen. Exemplary CpG oligonucleotides are described in U.S. Pat. Nos. 6,610,661; 6,589,940, and 6,514,948, the disclosures of which are incorporated herein for all purposes. CpG containing oligonucleotides interact with Toll-like receptors (such as TLR 7 and TLR9) and result in the production of interferon gamma (IFN-γ), which potentiates the antiviral immune response.

Additionally, some subjects (for example, aged subjects) who have reduced expression of TLRs can benefit from the co-expression of TLRs (such as TLR5, TLR7 and TLR9) in cells in which the adenovirus vector or adenovirus expressing the influenza antigen is expressed. Accordingly, adenovirus vectors containing a TLR can be included in the pharmaceutical compositions described above. A TLR can be incorporated into the same adenovirus vector that encodes the influenza antigen(s) or can be included in the pharmaceutical composition (medicament) as a separate adenovirus vector or virus. Optionally, a TLR and its ligand (e.g., a CpG oligonucleotide, flagellin) are included together in a pharmaceutical composition.

In certain embodiments, the pharmaceutical (e.g., vaccine compositions) are administered to avian subjects, such as domesticated fowl, including but not limited to, chickens, ducks, turkeys and geese. The pharmaceutical compositions can be administered to young and/or adult birds and/or to embryos in ovo. Methods utilized in the poultry industry for administering vaccine compositions are well known, and any such methods are suitable for administering the immunogenic compositions, e.g., adenovirus containing avian influenza antigen(s) disclosed herein. For example, adenovirus based influenza vaccines can be administered to domesticated fowl in drinking water. Various methods are available for administering vaccines in the drinking water of domesticated birds. In one convenient method, a solution containing the immunogenic composition is placed in an intravenous solution bag (for example, the SELECT FIELD BAG BOOST™ system from Merial, Inc., Lyon, France), which is connected to one or more drinker lines. Optionally, the solution contains a dye (or other visually detectable indicator, such as skimmed milk powder) along with the diluent to facilitate monitoring of vaccine administration. In the case of adenovirus-based vaccines, it is important that the solution be free of disinfecting agents, such as chlorine or other disinfectants that may be used to clean the delivery system. If desired, drinking activity of the birds can be stimulated to increase consumption of the vaccine/water solution. For example, by increasing light intensity, delivering food and/or disturbing the birds (e.g., by walking through the flock) birds can be stimulated to increase consumption of vaccine laden drinking water.

In another method, the vaccine composition is administered by spraying. Typically spray applications are performed on many birds housed in a common airspace, for example, spray administration can be performed on day old birds in delivery boxes, or to birds in conventional housing. For example, newly hatched birds can be vaccinated using a spray delivery system as described, e.g., in U.S. Pat. Nos. 6,713,073, 4,674,490 and 4,449,968, the disclosures of which are incorporated herein by reference. In one exemplary method, day old birds contained in delivery boxes in groups of up to approximately 150 subjects are exposed to vaccine diluted in an aqueous medium, such as water, delivered by means of a spray nozzle, which forms very small droplets (for example, in the range of approximately 100μ to about 500μ diameter). Vaccine is taken up by day old birds via the ocular, intranasal, as well as oral routes from the container surface and other birds. Vaccine can be delivered to older birds by spray administration, for example, using a pressurized spray apparatus or controlled droplet application device. A pressurized spray apparatus typically includes a pressure chamber, lance and nozzle. The nozzle and the operating pressure can be varied to alter the particle size, which is typically within a range of about 10μ to about 1000μ. Droplets come into contact with the birds either directly from nozzle emission via inhalation, or via ocular or oral routes, or indirectly from contact with vaccine deposited on the ground or other birds by the spray apparatus. Equipment for spray administration of vaccine compositions are readily available and exemplary devices are disclosed, e.g., in U.S. Pat. Nos. 5,312,353 and 4,863,443, the disclosures of which are incorporated herein by reference. Controlled droplet application devices developed for horticultural and insect control use can also be used to deliver adenovirus-based vaccine to domesticated fowl. In such devices, spray is generated by centrifugal force as the diluted vaccine is delivered to spinning disc which forms a spray of nebulized vaccine with a size range suitable for uptake by inhalation. This nebulized vaccine can be distributed by means of a fan which distributes the vaccine over a broader field than can typically be achieved with a pressurized spray apparatus. This process offers the added advantage that relatively small volumes of diluent (for example, water) are required. For example, up to 30,000 birds can be vaccinated with approximately one liter of vaccine solution.

More invasive and/or laborious procedures can also be employed to administer the immunogenic compositions disclosed herein to domesticated fowl, including, in addition to the methods disclosed above: eye drop, transfixion and scarification (e.g., via a cutaneous route in the wing web or foot), injection and in ovo administration. Automated and semi-automated injection devices suitable for delivering the disclosed vaccines to poultry are described, e.g., in U.S. Pat. Nos. 4,681,565 and 4,515,590, the disclosures of which are incorporated herein by reference.

In ovo administration of adenovirus containing avian influenza antigens is also favorably used to elicit a protective immune response against influenza in domestic fowl. In ovo administration typically involves injecting an immunologically effective dose of adenovirus containing one or more avian influenza virus antigens into eggs at an appropriate stage of gestation at which immunological competency has developed, but prior to hatching. For example, chicken eggs are typically injected at between 17.5 and 19 days of incubation. The volume is calculated to not substantially disrupt the integrity of the egg, and is typically in the range of between 0.01 and 0.1 ml (such as, 0.05 ml). Typically, a small hole is made in the shell of the egg, into which an injection needle is inserted to deliver the immunogenic composition. The injections can be performed manually or with the assistance of commercially-available automated equipment (such as that available from Embrex, Triangle Park, N.C.) used according to the manufacturer's instructions. Methods and equipment for in ovo administration of solutions to poultry eggs suitable for administering the vaccine compositions disclosed herein are disclosed in U.S. Pat. Nos. 4,903,635, 5,056,464, 5,136,979, 5,699,751, 5,900,929, 6,032,612, 6,244,214, and 6,981,470, the disclosures of which are incorporated herein by reference.

EXAMPLES

Example 1

Generation of Adenovirus Vector Expressing Avian Hemagglutinin (HA) Antigen

Homologous recombination was used to produce an exemplary adenovirus vector that expresses avian H5 hemagglutinin (HA) antigen. The Cre recombinase-mediated site specific recombination system of Ng et al. (*Human Gene Therapy* 10:2667-2672, 1999) was utilized to generate HAd5 vectors including an avian HA antigen. To generate a HAd5 E1 insertion vector expressing a HA antigen of a H5N1 strain influenza, the HA gene of strain A/Hong Kong/156/97 under the control of the cytomegalovirus immediate early promoter ("CMV promoter") was inserted at the StuI site in a shuttle vector (pDC311). The pDC311 shuttle vector is a plasmid that contains the left end of HAd5 (4 kb) with a 3.1 kb E1 deletion, a loxP site for site specific recombination in the presence of Cre recombinase, and an intact packaging signal ($\psi$). The resulting vector pDC311-H5 was cotransfected into 293 Cre (293 cells expressing Cre recombinase), along with pBHGloxΔE1,3Cre. The pBHGloxΔE1,3Cre plasmid contains almost the entire HAd5 genome with the exception of the packaging signal and deletions in the E1 and E3 region genes. This plasmid also includes a loxP site for Cre recombinase mediated recombination. When introduced together into 293 Cre cells Cre mediated recombination between the two plasmids generated the vector HAd5-HA (FIG. 1A).

Cell extracts analyzed by Western blotting exhibited expression of the introduced avian HA antigen (FIG. 1B).

Example 2

Immunogenicity and Efficacy of Protection in HAd-H5 Immunized Animals

To demonstrate immunogenicity of recombinant adenovirus expressing avian HA, mice were inoculated with recombinant adenovirus and challenged with a lethal dose of avian influenza virus. Twenty-five 6-8 week-old female C57BL/6 mice were randomly divided into 5 groups with 5 animals per group. The animals were inoculated intramuscularly on days 1 and 28 with either PBS, 15 µg recombinant H5 (hemagglutinin of avian H5N1 influenza virus expressed in baculovirus) without alum (H5 alone), 15 µg H5 with alum (H5+alum), $10^8$ p.f.u. of HAd-ΔE1E3 (HAd5 control vector), or $10^8$ p.f.u. of HAd-H5 (HAd5 vector expressing H5). Serum samples were collected on days 21 and 49 to monitor the development of H5-specific immune response by ELISA and micro-neutralization assay. Animals were challenged with $100 LD_{50}$ of H5N1 (A/Hong Kong/483/97) virus on day 70 and were monitored daily for gain or loss in body weight and obvious clinical signs of influenza infection.

A single inoculation of HAd-H5 elicited H5-specific IgG ELISA titers above 3.5 logs on day 21 demonstrating that H5 expressed by HAd5-H5 was highly immunogenic. Serum samples were collected on day 49 to monitor the development of H5N1 virus neutralizing antibody response by virus neutralization assay. Immunization of mice with HAd-H5 elicited H5N1-specific neutralizing antibody response similar to those obtained with a high dose of H5+alum (Table 1).

Figure 2:
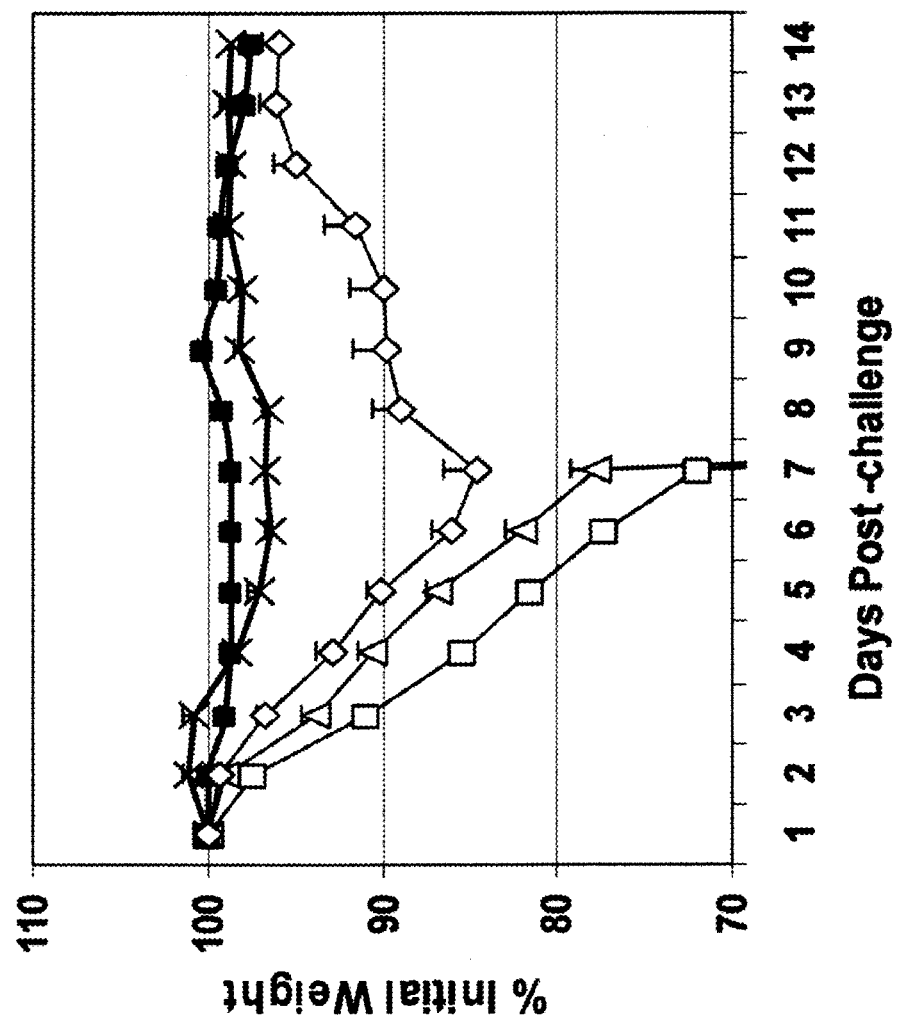
FIG. 2 is a line graph illustrating that the HAd-H5HA vector confers complete protection against challenge with a highly pathogenic homotypic H5N1 (A/HK/483/97) virus. Twenty-five (6- to 8-week-old) female BALB/c mice were randomly divided into 5 groups (5 animals/group) and inoculated intramuscularly on days 0 and 28 with either PBS (□), 10 µg of recombinant H5HA (hemagglutinin of avian HK/156/97 influenza virus expressed in baculovirus) without alum (◇), 10 µg of purified H5HA with alum (X), $10^8$ p.f.u. of HAd-ΔE1E3 (a), or $10^8$ p.f.u. of HAd-H5HA (■). The animals were challenged with 100 $LD_{50}$ of H5N1 (A/HK/483/97) virus on day 70. The mice were monitored for clinical signs and changes in body weights daily up to 14 days post-challenge.

Mice immunized with HAd-H5 were fully protected against morbidity and mortality following challenge with pathogenic H5N1 virus. Animals were challenged with 100 $LD_{50}$ of H5N1 (A/HK/483/97) virus on day 70. The level of protection was better than that observed with high dose recombinant H5+alum (Table 1 and FIG. 2). None of the mice in the HAd5-H5 showed any visual discomfort following challenge.

TABLE 1

Serological response in mice immunized with HAd-H5HA vaccines.

| Groups | Geometric Mean Horse HI titers | Geometric Mean Neutralization Titers | Survival |
|---|---|---|---|
| PBS | 25 | 20 | 0 |
| HAd-5 ($10^8$ p.f.u.) i.m. | 25 | 20 | 0 |
| HAd-H5HA ($10^8$ p.f.u.) i.m. | 696.4 | 2228 | 100 |
| rH5HA + alum i.m. | 696.4 | 2228 | 100 |
| rH5HA i.m. | 37.9 | 60 | 80 |

Example 3

Intranasal Administration of HAd5-HA Elicits Protective Immune Response

The ability of the HAd-H5HA vector to elicit an antibody response specific for HA was measured following intramuscular and intranasal administration. Three sets of 15 (6- to 8-week old) female BALB/c mice were randomly divided into 3 groups (5 animal/group) and inoculated intramuscularly on days 0 and 28 with $10^8$ p.f.u. of HAd-ΔE1E3 or $10^8$ p.f.u. of HAd-H5HA administered intramuscularly or intranasally. Sera were collected on days 21 and 49 to monitor the development of H5-specific immune response against A/HK/483/97, A/HK/213/03 and A/VN/1203/04 strains by hemagglutination inhibition (HI) assay using horse red blood cells. Intramuscular or intranasal administration of HAd5-H5HA elicited strong HA antibody titers by ELISA, as shown in Table 2.

TABLE 2

Titer against homologous and recent H5 strains induced by HAd5-HA vaccine

| Group | A/HK/156/97 | | A/HK/213/03 | | A/VN/1203/04 | |
|---|---|---|---|---|---|---|
| | $1^{st}$ bleed | $2^{nd}$ bleed | $1^{st}$ bleed | $2^{nd}$ bleed | $1^{st}$ bleed | $2^{nd}$ bleed |
| Vector Control | 5 | 5 | 5 | 5 | 5 | 5 |
| HAd5-H5 i.m. | 95 | 189 | 21.4 | 23.1 | 14.1 | 18 |
| HAd5-H5 i.n. | 146 | 218 | 36.4 | 36.4 | 18.2 | 18 |

Figure 3:
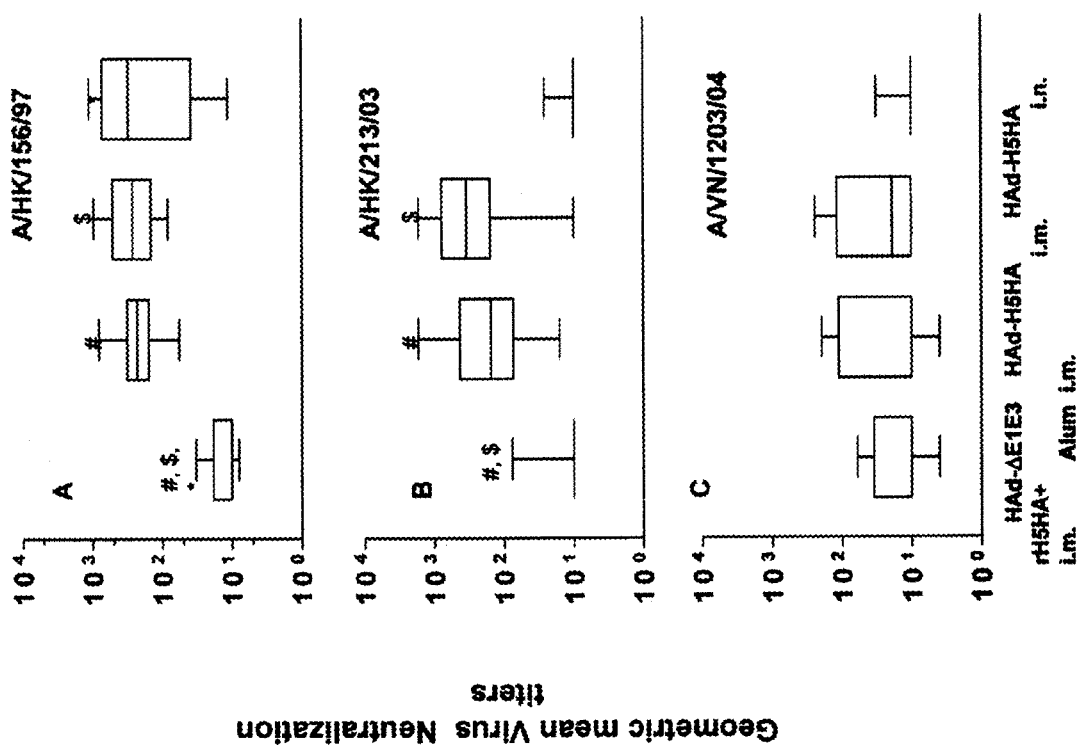
FIGS. 3A-C are Box-whisker plots showing mean, IQRs, and range of the neutralizing antibody response against homologous and heterologous avian influenza virus strains in mice immunized with HAd-H5HA vaccine. (A) HK/156/97, (B) HK/213/03, and (C) VN/1203/04 strains. *, # and $: differences between marked data are p=0.001. im=intramuscular immunization. in =intranasal immunization.

Similarly, virus neutralization assay BALB/c mice (20 per group) were immunized either intramuscularly or intranasally with $1 \times 10^8$ p.f.u. of HAd-H5HA twice every 4 weeks. Other groups of mice (20 per group) were intramuscularly immunized with $10^8$ p.f.u. of HAd-ΔE1E3 or 3 μg of rH5HA with alum. The serum samples were obtained 4 weeks after the second immunization and analysed by virus neutralization assays to assess their ability to react with a homologous virus (HK/156/97), or with antigenically heterologous viruses (A/Hong Kong/213/2003 [HK/213/03] and A/Vietnam/1203/04 [VN/1203/04]). Compared with HK/156/97, the amino acid homology in the hemagglutinin subunit is 94.8% for HK/213/03 and 95.5% for VN/1203/04. Exemplary results are shown in FIG. 3. Mice immunized with rH5HA+alum showed high virus neutralizing antibody titers against homologous HK/156/97 virus, but failed to neutralize HK/213/03 or VN/1203/04 virus. In contrast, mice immunized with HAd-H5HA produced neutralizing antibodies to both homologous and heterologous viruses, showing higher neutralizing antibody titers against HK/156/97 and lower titers against heterologous HK/213/03 or VN/1203/04 virus.

Example 4

Vaccination with HAd5-H5 elicits HA-specific T cell responses

Figure 4:
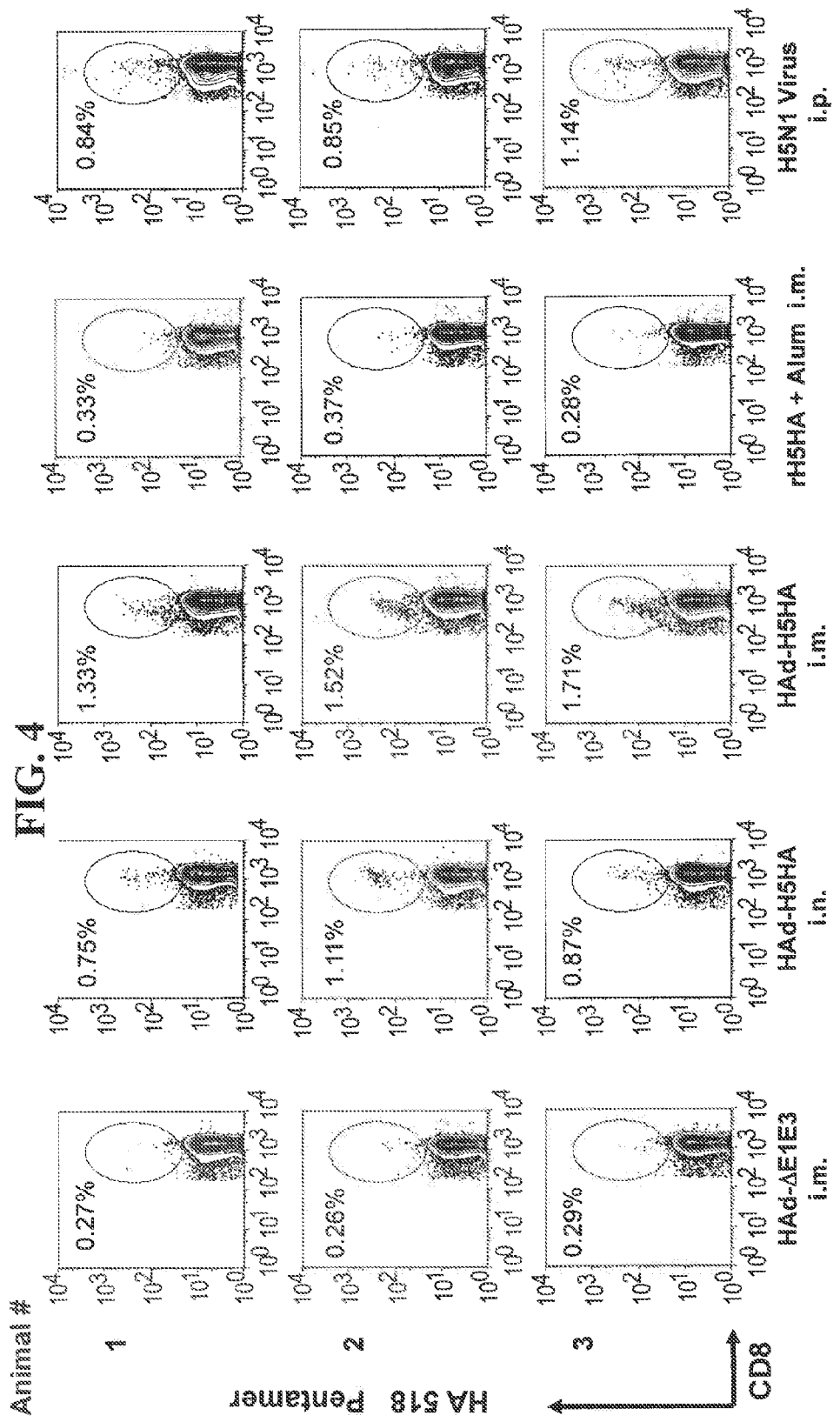
FIG. 4 is a series of scatter plots of flow cytometric analysis showing induction of HA-518-epitope-specific CD8 T cells in mice immunized with HAd-H5HA vaccine. Flow cytometric analysis of spleen cells from immunized mice (three per group) stained with HA 518 pentamer epitope. Pentamer-positive cells (circled) are shown as a percentage of CD8 T lymphocyte population.

To assess whether the HAd-H5HA vaccine induced an HA-specific CD8⁺ T cell response, BALB/c mice immunized with $10^8$ p.f.u. of HAd-ΔE1E3 or $10^8$ p.f.u. of HAd-H5HA administered intramuscularly or intranasally and splenic T cell responses to influenza epitopes were evaluated by staining with a $K_d$-specific pentamer for the immunodominant HA 518 ($HA_{518-526}$) epitope, originally described for HA of an H1N1 virus, A/Puerto Rico/8/34). This epitope is broadly conserved among H5N1 viruses, including currently circulating avian and human H5N1 viruses, as well as more divergent viruses, e.g., H9N2 strains. Mice that received the HAd-H5HA vector either i.n. or i.m. had at least a 3 to 8 fold higher frequency of HA-specific CD8⁺ T cells compared to the mice immunized with HAd-ΔE1E3 (FIG. 4). No detectable increase in NP-147 ($NP_{147-155}$)-epitope specific CD8⁺ T cells was observed in animals immunized with HAd-H5HA vaccine. In contrast, control mice infected with H5N1 virus exhibited a strong NP 147 epitope-specific CD8⁺ T cell response. None or the mice vaccinated with HAd-ΔE1E3 or rH5HA+alum showed an increase in HA 518 epitope-specific CD8⁺ T cell frequencies.

Figure 5:
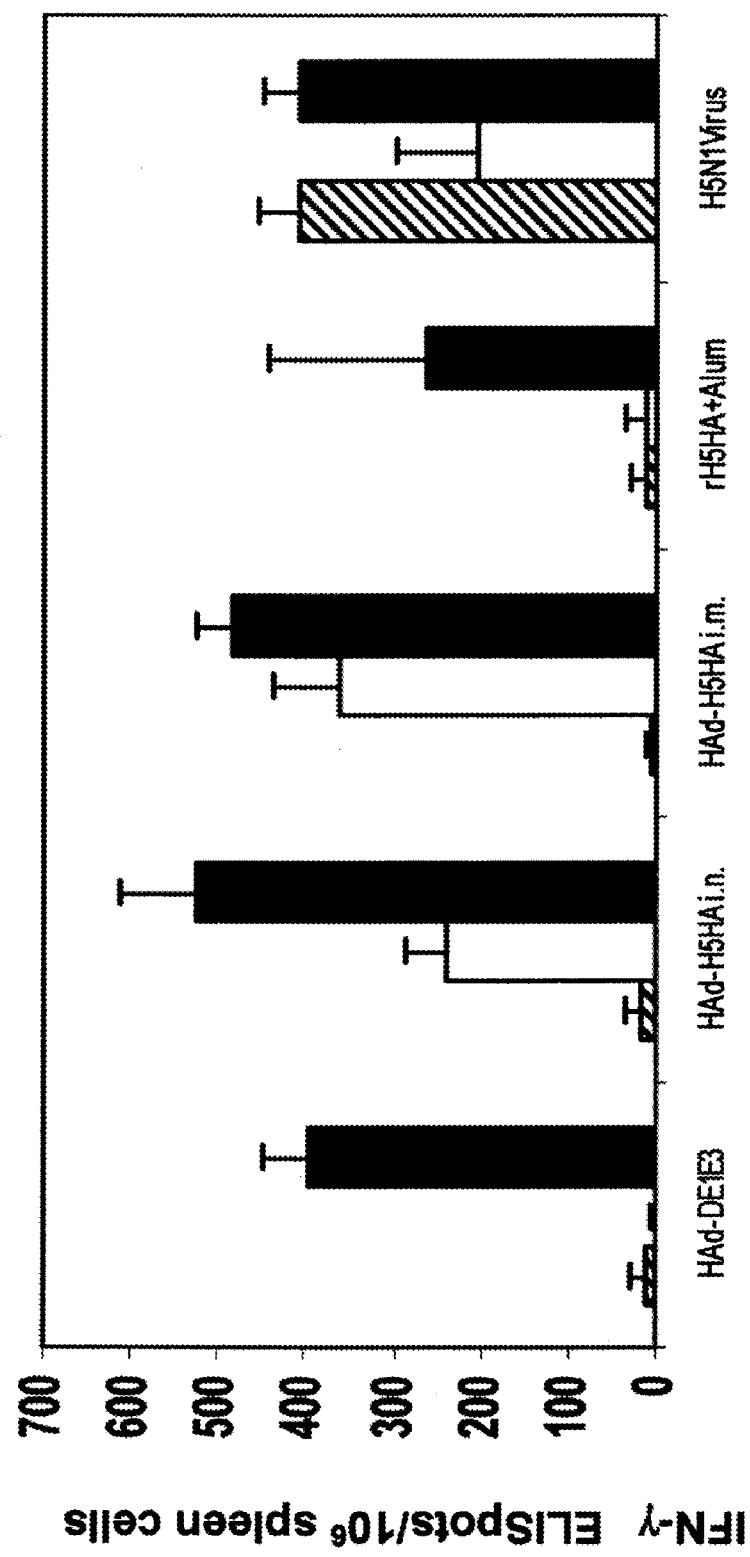
FIG. 5 is a bar graph illustrating interferon gamma secretion by HA-518-epitope-specific CD8 T cells. ELISpots measurements of interferon gamma in spleen cells of immunized mice. Data are mean and SDs (error bars). im=intramuscular immunization. in=intranasal immunization. Cultures were stimulated with $NP_{147-155}$ (diagonally hatched bars), HA (white bars), or phorbol myristate acetate (PMA)+ionomycin (black bars).

Epitope specific T cell responses were determined by stimulating $1 \times 10^6$ spleen cells with syngeneic gamma-irradiated spleen cells pulsed with 10 μg/ml of the designated peptide (including MHC Class I binding epitopes: NP 147 and HA 462 and HA 518, which have been shown to be dominant epitopes in H5N3 infected animals). PMA+ionomycin was used as a positive control. IFN-γ production was evaluated by ELIspot assay, as shown in FIG. 5. Vaccination with HAd5-H5 elicited HA-specific T cell responses against Class I MHC binding epitopes of HA. This T cell response was not observed in animals inoculated with recombinant H5+alum.

Example 5

Inoculation with HAd5-H5HA Confers Protection Against Lethal Challenge

Animals vaccinated with HAd5-H5HA by either intramuscular or intranasal administration routes were challenged with the homologous strain virus and with a recent strain of avian influenza. Following inoculation, mice were challenged with 100 $LD_{50}$ A/HK/156/97 or A/VN/1203/04 strain virus. As shown in Table 3, all inoculated animals survived lethal challenge with either the homologous virus or a different H5N1 virus strain.

TABLE 3

HAd-5H5HA confers protection against lethal challenge

| | % Survival against challenge with | |
|---|---|---|
| Group | A/HK/156/97 | A/VN/1203/04 |
| Vector Control | 0 | 0 |
| HAd-H5HA i.m. | 100 | 100 |
| HAd-H5HA i.n. | 100 | 100 |

Example 6

Morbidity of Animal Challenged with A/HK/483/97 or A/VN/1203/04 Virus

Figure 6:
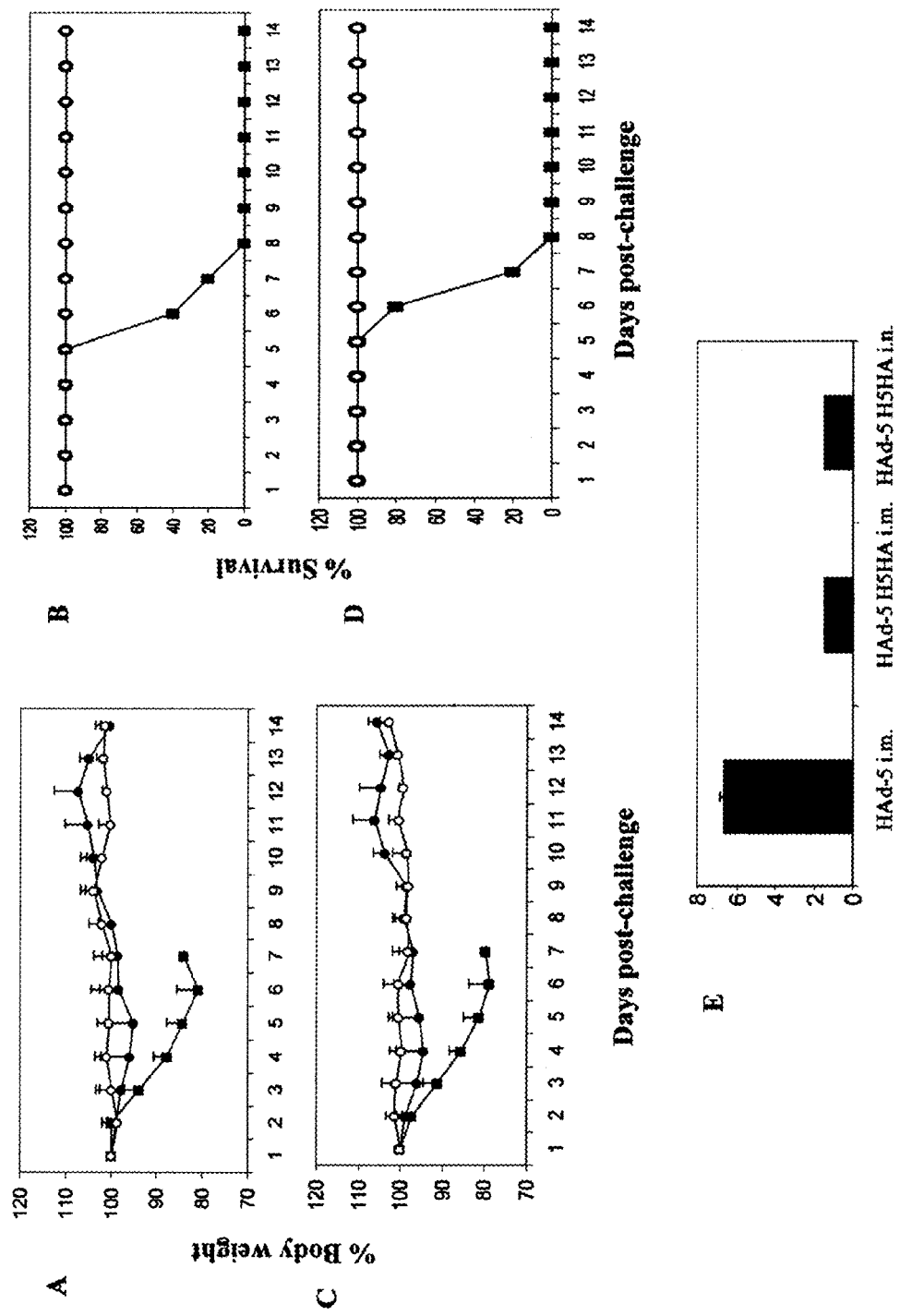
FIGS. 6A-D are line graphs and FIG. 6E is a bar graph illustrating protection against recent H5N1 viruses. BALB/C mice (15 animals/group) were inoculated intramuscularly (●) or intranasally (○) twice at a four weeks interval with $10^8$ p.f.u. of HAd-H5HA. HAd-ΔE1E3 (■) served as a negative control. Five animals from each group were challenged four weeks after the second immunization with 100 50% lethal dose ($LD_{50}$) of A/HK/483/97 (A and B) or A/VN/1203/04 (C and D) or 100 50% mouse infectious dose ($MID_{50}$) of A/HK/213/03 (E). The percent initial body weight (A and C) and survival post-challenge (B and D) are shown. Error bars depict the standard error of the mean. The mice challenged with A/HK/483/97 or ANN/1203/04 were monitored for clinical signs and changes in body weights daily up to 14 days post-challenge. The mice challenged with A/HK/213/03 were euthanized on day 3 post-challenge and lungs were collected. Tissues were frozen and thawed once, then homogenized in 1 mL PBS with antibiotics. Solid debris was pelleted by brief centrifugation before homogenates were titered for virus infectivity in 11-day old eggs.

To assess the protective efficacy against challenge with the variant H5N1 strains, mice immunized with HAd-H5HA were challenged with HK/483/97, HK/213/03 or VN/1203/04 viruses. Unlike the virulent HK/483/97 and VN/1203/04 strains, HK/213/03 virus is not highly lethal for mice. Therefore, to evaluate the vaccine efficacy against HK/213/03, virus titers in the lungs were measured in HK/213/03-infected animals on day 4 post-challenge. Immunization of mice either i.n. or i.m. with HAd-H5HA exhibited minimal morbidity and provided complete protection against death following challenge with HK/483/97 virus (FIGS. 6A and B). All mice vaccinated with HAd-H5HA by either route of inoculation survived and exhibited minimal morbidity, as measured by weight loss, following a lethal challenge with more recent H5N1 virus, VN/1203/04 (FIGS. 6C and D). Furthermore, mice vaccinated with HAd-H5HA by either route of inoculation and challenged with HK/213/03 virus had no detectable virus in the lungs on day 4 post-infection (FIG. 6E), whereas mice vaccinated with the control vector HAd-ΔE1E3 had a mean lung viral titer of greater than $10^6$ $EID_{50}$/ml (p<0.001).

Therefore, the HAd-H5HA vaccine induced significant protection against heterologous H5N1 viruses, even in the presence of low levels of cross-neutralizing serum antibody titers.

These data confirm the potential of Ad vector-based delivery of avian influenza antigen(s) as pandemic influenza vaccines. Such vectors induce strong humoral and cellular immunity and confer cross-protection against continuously evolving H5N1 viruses without the need of an adjuvant.

Example 7

Generation and Characterization of Nonhuman Vectors Expressing Ha of H5N1 Influenza Virus Infectious clones containing the entire genome of nonhuman adenovirus (porcine adenovirus type 3, PAd3 or bovine adenovirus type 3, BAd3) with deletions in E1 and E3 regions with or without insertion in E1 were generated by homologous recombination in *E. coli* BJ5183. The HA gene of H5N1, flanked by the CMV promoter and the bovine growth hormone BGH polyadenylation signal was cloned into pDS2 (Bangari & Mittal, *Virus Research* 105:127-136, 2004) at the AvrII site to obtain pDS2-H5. Using homologous recombination in *E. coli* BJ5183 as described in van Olphen & Mittal, *J. Virol. Methods* 77:125-129, 1999, with respect to bovine adenovirus, pPAd-H5 (a genomic plasmid with an avian HA insertion into the E1A gene region of porcine adenovirus) was generated by cotransformation of *E. coli* with E3-deleted PAd3 genomic DNA and StuI linearized pDS2-H5.

To generate HA of H5N1 influenza from the PAd3 vector, monolayer cultures of FPRT HE1-5 cells (an E1 expressing porcine cell line described in Bangari & Mittal, *Virus Res.* 105:127-136, 2004) were transfected with PacI-digested pPAd-H5 (5 µg/60-mm dish) using LIPOFECTIN®-mediated transfection according to the manufacturer's recommendations. Recombinant virus-induced cytopathic effect was visible in 2-3 weeks post-transfection.

Figure 7:
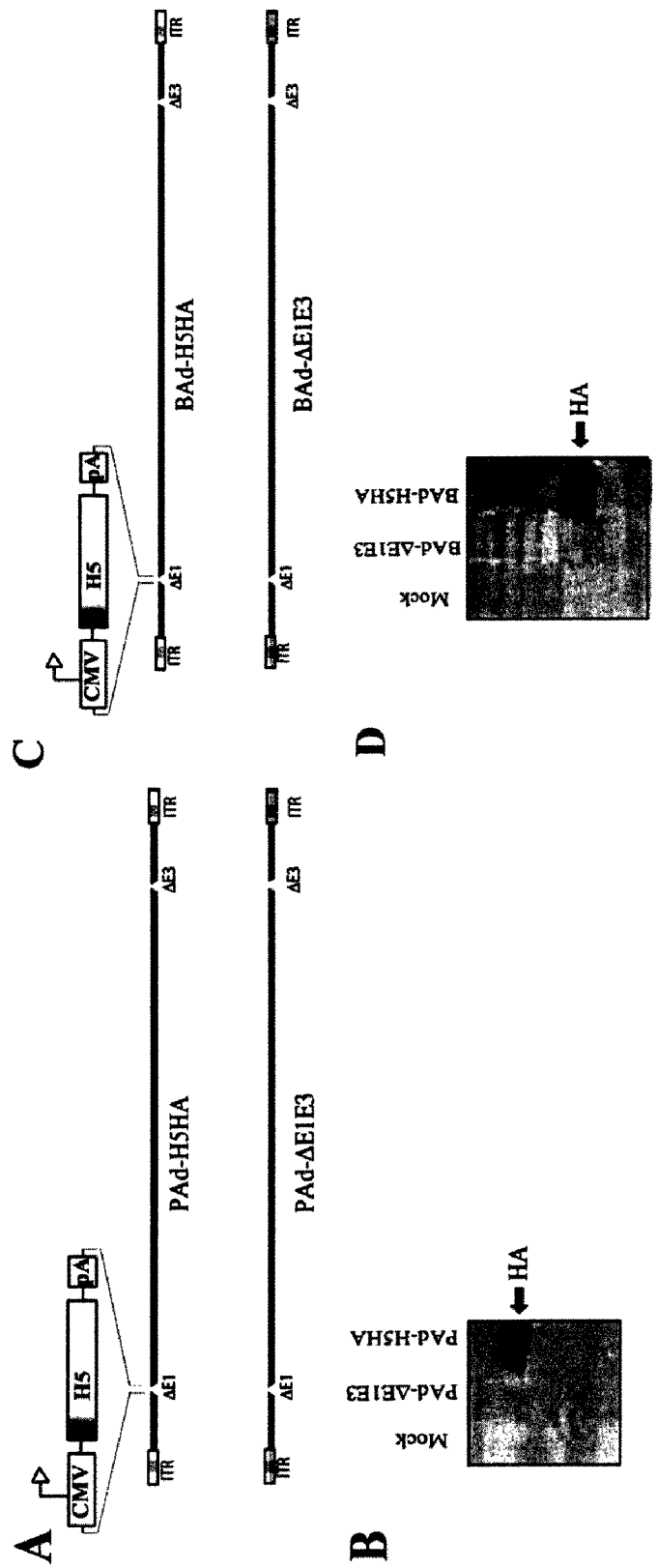
FIGS. 7A-D are schematic illustrations (A and C) and images of western blots (B and D) demonstrating expression of avian influenza hemagglutinin from porcine and bovine adenovirus vectors. PAd vector (PAd-H5HA) carrying the hemagglutinin subtype 5 (H5HA) gene of avian H5N1 influenza virus (A/HK/156/97) under the control of the cytomegalovirus (CMV) immediate early promoter inserted in the early region 1 (E1) of the PAd genome was generated. (A) Diagrammatic representation of structures of PAd vectors: PAd-ΔE1E3 (PAd with E1 and E3 deletions), and PAd-H5HA (PAd-ΔE1E3 with the H5HA gene cassette). ITR, inverted terminal repeat; ΔE1, deletion in E1; ΔE3, deletion in the E3; H5, H5HA; and pA, simian virus 40 polyadenylation signal. (B) FPRT HE1-5 cells were mock-infected or infected with PAd-ΔE1E3 or PAd-H5HA. At 24 h post-infection, cells were harvested and cell extracts were analyzed by Western blot using a rabbit hyperimmune serum against H5HA. BAd vector (BAd-H5HA) carrying the hemagglutinin subtype 5 (H5HA) gene of avian H5N1 influenza virus (A/HK/156/97) under the control of the cytomegalovirus (CMV) immediate early promoter inserted in the early region 1 (E1) of the BAd genome was generated. (C) Diagrammatic representation of structures of BAd vectors: BAd-ΔE1E3 (PAd with E1 and E3 deletions), and BAd-H5HA (BAd-ΔE1E3 with the H5HA gene cassette). ITR, inverted terminal repeat; ΔE1, deletion in E1; ΔE3, deletion in the E3; H5, H5HA; and pA, simian virus 40 polyadenylation signal. (D) FBRT-HE1 cells were mock-infected or infected with BAd-ΔE1E3 or BAd-H5HA. At 24 h post-infection, cells were harvested and cell extracts were analyzed by Western blot using a rabbit hyperimmune serum against H5HA.

Replication-defective recombinant PAd3 vector (PAd-H5HA) containing the full-length coding region of the HA gene of H5N1 virus (HK/156/97) inserted in the early region 1 (E1) of PAd3 genome (FIG. 7A) was expressed efficiently in FPRT HE1-5 cells as demonstrated by western blotting (FIG. 7B). A PAd with deletions of E1 and E3 regions (PAd-ΔE1E3) served as a negative control.

Similarly, a replication-defective recombinant BAd3 vector (BAd-H5HA) including the full-length coding region of the HA gene of H5N1 virus (HK/156/97) inserted in the early region 1 (E1) of BAd3 genome (FIG. 7C) was expressed efficiently in FBRT-HE1 cells that express BAd3 E1 (van Olphen et al., *Virology* 295:108-118, 2002) as shown in FIG. 7D. A BAd3 with deletions of E1 and E3 regions (BAd-ΔE1E3) served as a negative control.

These nonhuman adenoviral vectors are suitable as vaccine vectors, which can be administered to human and non-human subjects to elicit a protective immune response specific for avian (and other) influenza strains.

Example 8

Cell Lines for Expressing Adenovirus Vectors

Novel cell lines were produced that express E1 antigens of adenovirus vectors with different species tropism (human and non-human). Such multi-functionality cell lines are particularly advantageous for optimizing production of replication deficient adenovirus from recombinant vectors corresponding to viruses from multiple strains to produce adenovirus and/or recombinant protein.

Two exemplary multi-functionality cell lines were produced, based on previously described cell lines that express the HAd5 E1 gene in either bovine or porcine cells. FBRT-HE1 is a fetal bovine retinal cell line that expresses the E1 gene of the human adenovirus strain HAd5 (SEQ ID NO:4). Construction and isolation of the FBRT-HE1 cell line is disclosed in van Olphen et al., (*Virology* 295:108-118, 2002), which is incorporated herein by reference. In brief, primary fetal bovine retina (FBRT) cells were transfected with the plasmid containing HAd5 E1 (where HAd5 E1 was under the control of the PGK promoter). A number of G418-resistant colonies were isolated and tested for the expression of E1B-19 kDa protein by Western blot. Cell lines expressing E1B-19kDa were further tested for E1A, E1B-19 kDa and E1B-55 kDa expression by immunoprecipitation. A representative cell line, designated FBRT-HE1, expressed all three E1 proteins: E1A, E1B-19kDa and E1B-55 kDa. The FBRT-HE1 cell line supports the growth of E1-deleted human adenovirus vectors as well as E1 deleted bovine adenovirus vectors.

Figure 8:
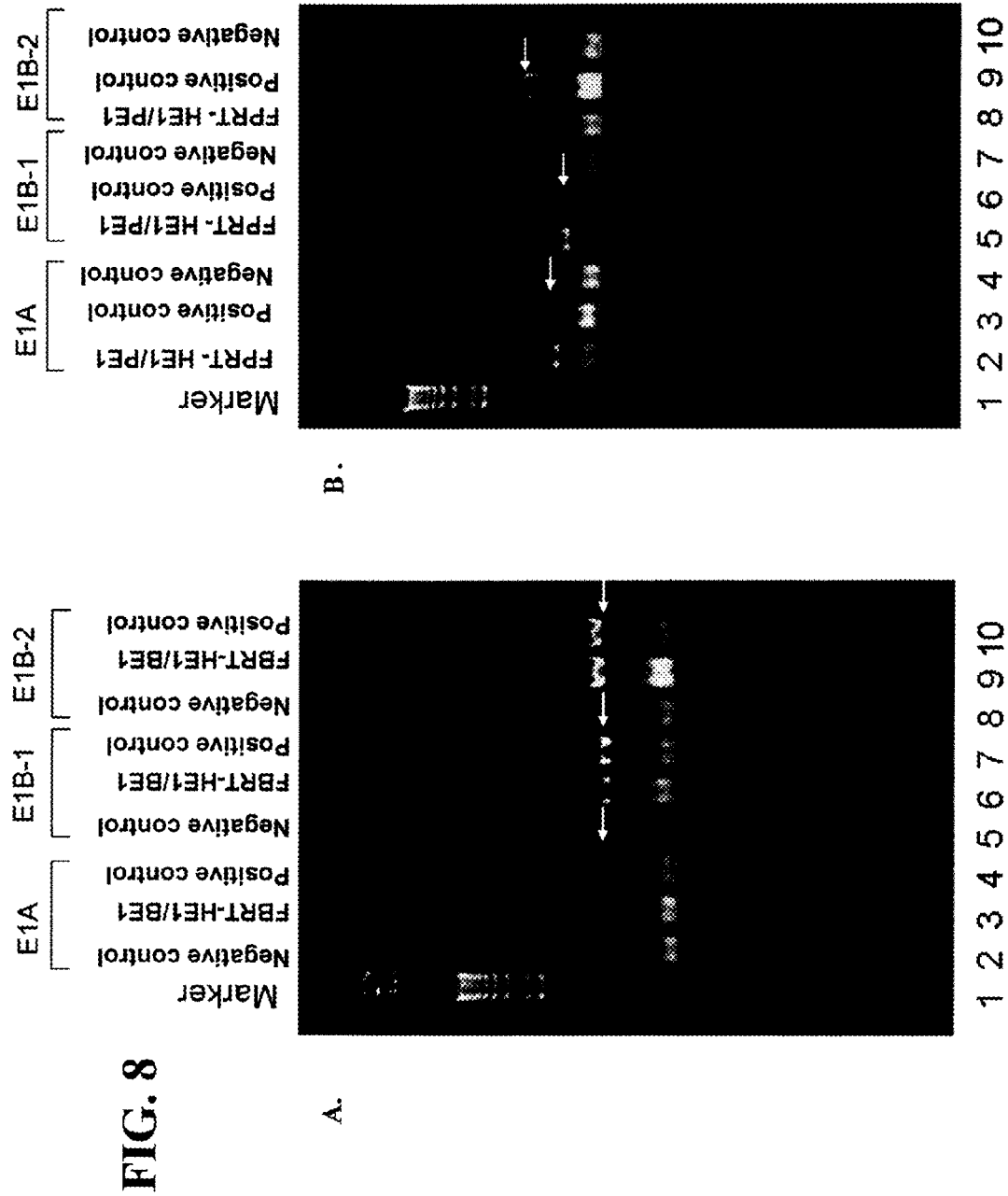
FIGS. 8A and B are images showing expression of bovine and porcine E1 genes in transfected cells. (A) Expression of BAd3 E1A, E1B-19 kDa (E1B-1), and E1B-55 kDa (E1B-2) messages as detected by RT-PCR using specific primer sets. (B) Expression of PAd3 E1A, E1B-19 kDa (E1B-1), and E1B-55 kDa (E1B-2) messages as detected by RT-PCR using specific primer sets. Specific bands are shown by arrows.

To produce a multi-functionality cell line, a fragment containing BAd3 E1 (604-3148) was amplified using BAd E1-F (CCATGAAGTACCTGGTCCTC; SEQ ID NO:5) and BAd E1-R (CCCCACCTATTTATACCCCTC; SEQ ID NO:6) primer set. The PCR fragment encompassing the BAd3 E1 gene (SEQ ID NO:7) was cloned in pPGK-puro at the EcoRV site and in pCMV-puro at the KpnI-XbaI site to obtain pPGK-BE1 and pCMV-BE1, respectively. These plasmids were then used to transfect FBRT-HE1 cells using Lipofectin (Life Technologies). After 48 hrs of transfection the cells were grown in the selection media containing 3 µg/ml puromycin. Discreet colonies of cells could be seen after about 30 days of antibiotic selection in pPGK-BE1 or pCMV-BE1 transfected FBRT-HE1 cells. 24 colonies (12 colonies each from pPGK-BE1 and pCMV-BE1 transfected cells) were picked, expanded and screened for expression of all three BAd3 E1 transcripts (E1A, E1B-1 and E1B-2) by RT-PCR using the specific primer sets (Table 4) to identify clones that expressed all three BAd E1 transcripts. The FBRT-HE1/PE1 cell clone shown in FIG. 8A illustrates expression of all three BAd3 E1 genes under the PGK promoter.

TABLE 4

Primers for RT PCR of bovine E1 transcripts

| Gene | Primer sequence (5' to 3') |
|---|---|
| BAd E1A (For) | (SEQ ID NO: 8)<br>CTGATATCATGAAGTACCTGGCCTC |
| BAd E1A (Rev) | (SEQ ID NO: 9)<br>ATGCAATGGTAGGTTTGG |
| BAd E1B-1 (For) | (SEQ ID NO: 10)<br>GATATCATGGATCACTTAAGCGTTC |
| BAd E1B-1 (Rev) | (SEQ ID NO: 11)<br>GTCGACAACTGATGTGCTCGAAACG |
| BAd E1B-2 (For) | (SEQ ID NO: 12)<br>GATATCGTTCAAGATCACCCAGAG |
| BAd E1B-2 (Rev) | (SEQ ID NO: 13)<br>GTCGACCACTTTTAATCCTGCTC |

Similarly, multi-functional porcine cells were produced by introducing a porcine adenovirus E1 (PAd3 E1) into a cell line that expressed HAd5 E1. FPRT-HE1-5 is a fetal porcine retinal cell line that constitutively expresses the HAd5 E1 (SEQ ID NO:4). Production of FPRT-HE1-5 is disclosed in Bangari & Mittal (*Virus Res.* 105:127-136, 2004), which is incorporated herein by reference. In brief, primary fetal porcine retinal (FPRT) cells were transfected with a plasmid containing HAd5 E1 under the control of either the cytomegalovirus (CMV) immediate early or phosphoglycerate kinase (PGK) promoter. Transformed cell lines obtained by transfection with HAd5 E1 sequences under the control of CMV or PGK promoter were selected and further characterized. FPRT-HE1-5 is an exemplary cell line that expresses all three E1 genes efficiently and can be used to generate and grow E1-deleted porcine and human adenovirus vectors.

PAd3 plasmids were constructed for transfection into FPRT-HE1-5 cells in the following manner. The neomycin ORF in the pcDNA3.1 (Invitrogen) was replaced with puromycin ORF from pBABE-puro (Addgene) to obtain the plasmid pCMV-puro. The CMV promoter sequence in plasmid pcDNA3.1-puro was replaced with PGK promoter from pGT-N28 (New England Biolabs) to obtain the plasmid pPGK-puro. The fragments containing PAd3 E1 (526-3259) was amplified using PAd E1-F (TGGATCCTCGACATGGC-GAACAGACTT; SEQ ID NO:14) and PAd E1-R (TCTC-GAGTCATCCTCAGTCATCGTCATCG; SEQ ID NO:15) primer set. The resulting PCR product including the coding sequence of the PAd3 E1 gene (SEQ ID NO:16) was subsequently cloned at the BamHI-XhoI site of pPGK-puro or pCMV-puro to obtain pPGK-PE1 and pCMV-PE1, respectively.

These plasmids were then used to transfect FPRT-HE1 cell line using Lipofectin (Life Technologies). After 48 hrs of transfection the cells were grown in the selection media containing 2 μg/ml puromycin. Discreet colonies of cells could be seen after about 30 days of antibiotic selection in both pPGK-PE1 and pCMV-PE1 transfected FPRT-HE1 cells. Twenty-four colonies (12 colonies each from pPGK-PE1 and pCMV-PE1 transfected cells) were picked, expanded and screened for expression of all three PAd3 E1 transcripts (E1A, E1B-1 and E1B-2) by RT-PCR using the specific primer sets (Table 5). Multiple clones from pPGK-PE1 transfected cells and pCMV-PE1 transfected cells were found positive for expression of all three PAd3 E1 transcripts. The FPRT-HE1/PE1 cell clone shown in FIG. 8B illustrates E1 expression under the PGK promoter.

TABLE 5

Primers for RT PCR of porcine E1 transcripts

| Gene | Primer sequence (5' to 3') |
|---|---|
| PAd E1A (For) | (SEQ ID NO: 17) AGGTGGAGGTGATTGTGACTGA |
| PAd E1A (Rev) | (SEQ ID NO: 18) GACGCAAGAGGAAGTACTGCTA |
| PAd E1B-1 (For) | (SEQ ID NO: 19) CTGGCCAAGCTTACTAACGTGAAC |
| PAd E1B-1 (Rev) | (SEQ ID NO: 20) TTTAAGTCTTCTGGTGCCGCCA |
| PAd E1B-2 (For) | (SEQ ID NO: 21) ATGCATGAGCGCTACAGCTTTG |
| PAd E1B-2 (Rev) | (SEQ ID NO: 22) CTGAGTTCCGCAAGAATGTGCT |

Example 9

Adenovirus Vectors Expressing Multiple Influenza Antigens

Multiple Influenza Antigens

Adenovirus vectors are generated that incorporate multiple (a plurality of) influenza antigens. The Cre recombinase-mediated site specific recombination system of Ng et al., (*Human Gene Therapy* 10:2667-2672, 1999) can be utilized to generate HAd5 vectors including two or more influenza antigens. To generate a HAd5 E1 insertion vector expressing multiple influenza antigens, polynucleotide sequences that encode the selected antigens are cloned under the control of a promoter, such as the cytomegalovirus immediate early promoter ("CMV promoter"), and inserted, e.g., at the StuI site in a shuttle vector. The shuttle vector, such as pDC311, includes a loxP site for site specific recombination in the presence of Cre recombinase, and an intact packaging signal (ψ). The resulting vector is cotransfected into 293 Cre (293 cells expressing Cre recombinase), along with pBHGloxΔE1,3Cre. The pBHGloxΔE1,3Cre plasmid contains almost the entire HAd5 genome with the exception of the packaging signal and deletions in the E1 and E3 region genes. This plasmid also includes a loxP site for Cre recombinase mediated recombination. When introduced together into 293 Cre cells Cre mediated recombination between the two plasmids generates a vector that includes the polynucleotide sequence encoding the selected influenza antigens. Optionally, this procedure can be used to incorporate a polynucleotide sequence that encodes an additional polypeptide that augments immune function, such as the TLRs described above. Exemplary combinations of influenza antigens are provided in Table 6. The exemplary combinations given in Table 6 are meant to be illustrative. Additional combinations of antigens can be determined by those of ordinary skill in the art. Similarly, non-human adenovirus vectors (e.g., PAd3 or BAd3) can be used to generate various recombinants expressing the exemplary combinations of influenza antigens are provided in Table 6.

TABLE 6

Exemplary combinations of antigens in multi-antigen adenovirus vectors.

| Exemplary Combination | Hemagglutinin (HA) | Neuraminidase (NA) | Internal Protein(s) |
|---|---|---|---|
| 1 | H5 | N1 | (—) |
| 2 | H7 | N7 | (—) |
| 3 | H9 | N2 | (—) |
| 4 | H5 | N1 | M* |
| 5 | H7 | N7 | M |
| 6 | H9 | N2 | M |
| 7 | H5 | N1 | NP |
| 8 | H7 | N7 | NP |
| 9 | H9 | N2 | NP |
| 10 | H5 | N1 | M + NP |
| 11 | H7 | N7 | M + NP |
| 12 | H9 | N2 | M + NP |
| 13 | H5 | N1 | NS1 |
| 14 | H7 | N7 | NS1 |
| 15 | H9 | N2 | NS1 |
| 16 | H5 | | M |
| 17 | H5 | | NP |
| 18 | H5 | | M + NP |
| 19 | H7 | | M |
| 20 | H7 | | NP |
| 21 | H7 | | M + NP |

TABLE 6-continued

Exemplary combinations of antigens
in multi-antigen adenovirus vectors.

| Exemplary Combination | Hemagglutinin (HA) | Neuraminidase (NA) | Internal Protein(s) |
|---|---|---|---|
| 22 | H9 | | M |
| 23 | H9 | | NP |
| 24 | H9 | | M + NP |
| 25 | H5[1] + H5[2] + H5[3] | | |
| 26 | H5[1] + H5[2] + H5[3] | N1 | |
| 27 | H5[1] + H5[2] + H5[3] | | M |
| 28 | H5[1] + H5[2] + H5[3] | | NP |
| 29 | H5[1] + H5[2] + H5[3] | | M |
| 30 | H5[1] + H5[2] + H5[3] | N1 | NP |
| 31 | H5[1] + H5[2] + H5[3] | N1 | M + NP |
| 32 | H5 + H7 + H9 | | |
| 33 | H5 + H7 + H9 | N1 | |
| 34 | H5 + H7 + H9 | | M |
| 35 | H5 + H7 + H9 | | NP |
| 36 | H5 + H7 + H9 | | M |
| 37 | H5 + H7 + H9 | N1 | NP |
| 38 | H5 + H7 + H9 | N1 | M + NP |

Superscript designations indicate variants.
*M indicates either M1, M2 or both M1 and M2.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An isolated recombinant adenovirus vector comprising a first heterologous polynucleotide sequence that encodes more than one avian influenza surface or envelope protein antigen from influenza strain H5, H7 and/or H9 and a second heterologous polynucleotide sequence that encodes at least one influenza internal protein.

2. The isolated recombinant adenovirus vector of claim 1, wherein one of the avian influenza surface or envelope protein antigens comprises an avian influenza hemagglutinin (HA) antigen.

3. The isolated recombinant adenovirus vector of claim 1, wherein the first heterologous polynucleotide sequence encodes a plurality of variants of the same HA antigen subtype selected from group consisting of H5, H7 and H9.

4. The isolated recombinant adenovirus vector of claim 1, wherein the first heterologous polynucleotide sequence encodes a plurality of HA antigens of different HA subtypes selected from group consisting of H5, H7 and H9.

5. The isolated recombinant adenovirus vector of claim 1, wherein one of the avian influenza surface or envelope protein antigens comprises an avian influenza neuraminidase (NA) antigen.

6. The isolated recombinant adenovirus vector of claim 1, wherein one of the avian influenza surface or envelope protein antigens comprises an H5N1 strain antigen, an H7N7 strain antigen, or an H9N2 strain antigen.

7. The isolated recombinant adenovirus vector of claim 1, wherein the influenza internal protein is an M1 protein, an M2 protein, an NP protein, an PB1 protein, a PB2 protein, an NS1 protein, an NS2 protein, or a combination thereof.

8. The isolated recombinant adenovirus vector of claim 1, wherein the internal protein is of an H1N1, H2N2 or H3N2 influenza strain.

9. An immunogenic composition comprising the isolated recombinant adenovirus vector of claim 1.

10. The immunogenic composition of claim 9, further comprising a pharmaceutically acceptable carrier.

11. The isolated recombinant adenovirus vector of claim 1, wherein the adenovirus vector is a human adenovirus vector.

12. The isolated recombinant adenovirus vector of claim 1, wherein the adenovirus vector is a replication defective adenovirus vector.

13. The isolated recombinant adenovirus vector of claim 12, wherein the replication defective adenovirus comprises a mutation in at least one of an E1 region gene and an E3 region gene.

14. The isolated recombinant adenovirus vector of claim 1, wherein the adenovirus vector is replication competent.

15. The isolated recombinant adenovirus vector of claim 1, wherein the adenovirus vector is a non-human adenovirus vector.

16. The isolated recombinant adenovirus vector of claim 15, wherein the non-human adenovirus vector is a porcine adenovirus vector, a bovine adenovirus vector, a canine adenovirus vector, a murine adenovirus vector, an ovine adenovirus vector, an avian adenovirus vector or a simian adenovirus vector.

17. A method of producing an immune response against an avian influenza virus infection in a subject, the method comprising:

administering to a subject the immunogenic composition of claim 9, thereby producing the immune response against the avian influenza virus infection in the subject.

18. The method of claim 17, wherein the immune response is a protective or partially protective immune response against one or more avian influenza virus.

19. The method of claim 17, comprising administering the immunogenic composition intranasally, orally, ocularly, intravenously, intramuscularly, transdermally, intradermally, or subcutaneously.

20. The method of claim 17, wherein the subject is a human subject.

21. The method of claim 17, wherein the subject is a bird.

* * * * *